(12) United States Patent
Brain et al.

(10) Patent No.: US 8,552,015 B2
(45) Date of Patent: Oct. 8, 2013

(54) QUINAZOLINONE DERIVATIVES AND THEIR USE AS CB AGONISTS

(75) Inventors: Christopher T Brain, London (GB); Edward K Dziadulewicz, London (GB); Terance W Hart, London (GB)

(73) Assignee: Novartis AG, Basel (CH)

( * ) Notice: Subject to any disclaimer, the term of this patent is extended or adjusted under 35 U.S.C. 154(b) by 1578 days.

(21) Appl. No.: 11/823,315

(22) Filed: Jun. 26, 2007

(65) Prior Publication Data

US 2007/0265285 A1    Nov. 15, 2007

Related U.S. Application Data

(63) Continuation of application No. 10/503,779, filed as application No. PCT/EP03/01140 on Feb. 5, 2003, now abandoned.

(30) Foreign Application Priority Data

| Feb. 6, 2002 | (GB) | 0202755.5 |
| Jun. 10, 2002 | (GB) | 0213285.0 |
| Sep. 16, 2002 | (GB) | 0221459.1 |
| Sep. 16, 2002 | (GB) | 0221460.9 |

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC ........................ 514/266.3; 544/287

(58) Field of Classification Search
USPC ........................ 514/266.3; 544/287
See application file for complete search history.

(56) References Cited

U.S. PATENT DOCUMENTS

| 3,652,567 | A | 3/1972 | Boltze et al. |
| 4,276,295 | A | 6/1981 | Ishikawa et al. |
| 4,451,467 | A | 5/1984 | Ishikawa et al. |
| 6,017,919 | A | 1/2000 | Inaba et al. |
| 2008/0004296 | A1 * | 1/2008 | Charman et al. ........... 514/266.3 |

FOREIGN PATENT DOCUMENTS

| EP | 0 056 637 B1 | 7/1982 |
| FR | 6 200 M | 7/1968 |
| FR | 2 444 671 A | 7/1980 |
| GB | 2 040 927 A | 9/1980 |
| WO | WO 93/23082 A1 | 11/1993 |
| WO | WO 97/29079 A1 | 8/1997 |
| WO | WO 03/066603 A1 | 8/2003 |
| WO | WO 2005/058326 A1 | 6/2005 |

OTHER PUBLICATIONS

Ishikawa, M. et al., "New Hypotensive Agent", Chemical and Pharmaceutical Bulletin, vol. 30, No. 2, pp. 744-749, (1982).

Anikwue, R. et al., "Decrease in Efficacy and Potency . . . ", J. Pharm. & Expr. Ther., 2002, vol. 303, No. 1, pp. 340-346.

Emil, P. "Trends in Neuroprotection", Archivos de la Sociedad Espanola de Oftalmologia, Jun. 2002, No. 6, p. 1.

Ploner, C.J. et al., "Oculomotor Effects of d-9-Tetrahydrocannabinol in Humans . . . ", Cerebral Cortex, Oct. 2002, vol. 12, No. 10, pp. 1016-1023.

Rawls, S.M., "N-Methyl-D-aspartate Antagonists . . . ", J. Pharm. & Expr. Ther., 2002, vol. 303, No. 1, pp. 395-402.

Ulfers, A.L., "Cannabinoid receptor-G protein interactions . . . ", Protein Science, 2002, vol. 11, pp. 2526-2531.

Eguchi et al., "Synthetic Studies of Antiatherogenic Agesnts (VII) Syntheses of Methylcarbamate of Substituted Quinazolinones", Reports of the Institute for Medical & Dental Engineering, vol. 11 (1977), pp. 55-59.

Eguchi et al., "Synthetic Studies of Substituted Quinazolinone", Reports of the Institute for Medical & Dental Engineering, vol. 23 (1989), pp. 65-72.

Ishikawa et al, "Syntheses of 2-Hydroxymethyl-4 (3H)-Quinazoline and its Analogs", Heterocycles, vol. 16, No. 1 (1981), pp. 31-34.

Methaqualone—Wikipedia, the free encyclopedia, "Methaqualone", [online], [retrieved on Jan. 12, 2010], retrieved from http://en.wikipedia.org/wiki/Methaqualone, 4 pgs.

Christine Charman, U.S. PTO Office Action, U.S. Appl. No. 11/570,393, Sep. 28, 2010, 12 pgs.

Dua et al., "Antitussive activity of some 2,3 di-substituted quinazolones", Indian Journal of Medical Research, vol. 54, No. 1 (1967), pp. 55-59.

Dua et al., "Spasmolytic activity of some newer quinazolones", Indian Journal of Physiology and Pharmacology, vol. 11, No. 3 (1967), pp. 107-111.

Morita et al., "Antitussive effect of WIN 55212-2, a cannabinoid receptor agonist", European Journal of Pharmacology, vol. 474, No. 2-3 (2003), pp. 269-272.

Patel et al., "Inhibition of guinea-pig and human sensory nerve activity and the cough reflex in guinea-pigs by cannabinoid ($CB_2$) receptor activation", British Journal of Pharmacology, vol. 140, No. 2 (2003), pp. 261-268.

* cited by examiner

*Primary Examiner* — Paul V. Ward
(74) *Attorney, Agent, or Firm* — Paul D. Strain, Esq.; Strain & Strain PLLC

(57) ABSTRACT

Novel quinazolinone derivatives of formula I

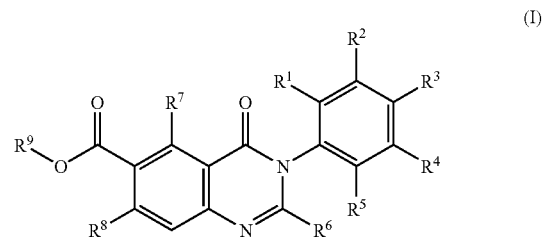

(I)

wherein $R^1$-$R^9$ are as defined in the description, processes for their production, their use as pharmaceuticals and pharmaceutical compositions comprising them.

6 Claims, No Drawings

QUINAZOLINONE DERIVATIVES AND THEIR USE AS CB AGONISTS

This is a continuation of Application No. 10/503,779 filed on Aug. 6, 2004, now abandoned which is National Stage of International Application No. PCT/EP03/01140 filed on Feb. 5, 2003, the entire disclosures of which are hereby incorporated by reference.

The present invention relates to novel quinazolinone derivatives, to processes for their production, their use as pharmaceuticals and to pharmaceutical compositions comprising them.

More particularly the present invention provides in a first aspect, a compound of formula I

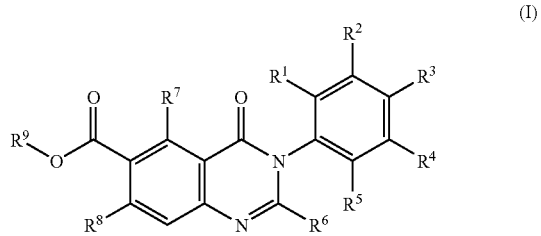

wherein $R^1$ $R^2$, $R^3$, $R^4$ and $R^5$ independently are hydrogen; halogen; $C_1$-$C_4$alkyl; $C_2$-$C_4$alkenyl; $C_3$-$C_7$cycloalkyl; $C_3$-$C_7$cycloalkyl$C_1$-$C_4$alkyl; $C_1$-$C_4$alkoxy$C_1$-$C_4$alkyl; $C_1$-$C_4$alkylcarboxy; hydroxy$C_1$-$C_4$alkoxy$C_1$-$C_4$alkyl; hydroxy; hydroxy$c_1$-$C_4$alkyl; phenyl$C_1$-$C_4$alkyl which is optionally substituted by hydroxy, $C_1$-$C_4$alkoxy, carboxy, $C_1$-$C_4$alkoxycarbonyl$C_1$-$C_4$alkyl, $C_1$-$C_4$alkoxycarbonyl, cyano; —$SO_2R^{10}$; cyano; —$SO_2N(R^{10})R^{11}$; —S—$R^{10}$ or —$SOR^{10}$; or $R^1$ and $R^2$ or $R^2$ and $R^3$ denote, together with the carbon atoms to which they are attached, an aromatic or aliphatic carbocyclic group having 5 to 10 ring atoms or an aromatic or aliphatic heterocyclic group having 5 to 10 ring atoms of which one, two or three are hetero atoms selected from nitrogen, oxygen and sulfur;

$R^6$ is —$CH_2$—O—C(O)—N($R^{12}$)$R^{13}$, —$CH_2$—X—C(O)—$R^{14}$, $C_1$-$C_4$alkyl or hydroxy$C_1$-$C_4$alkyl;

$R^7$, $R^8$ and $R^9$ independently are $C_1$-$C_4$alkyl;

$R^{10}$ and $R^{11}$ independently are hydrogen, $C_1$-$C_4$alkyl; $C_2$-$C_4$alkenyl; $C_3$-$C_7$cycloalkyl; $C_3$-$C_7$cycloalkyl$C_1$-$C_4$alkyl; $C_1$-$C_4$alkoxy$C_1$-$C_4$alkyl; $C_1$-$C_4$alkylcarboxy; hydroxy$C_1$-$C_4$alkoxy$C_1$-$C_4$alkyl; hydroxy; hydroxy$C_1$-$C_4$alkyl; phenyl$C_1$-$C_4$alkyl which is optionally substituted by hydroxy, $C_1$-$C_4$alkoxy, carboxy, $C_1$-$C_4$alkoxycarbonyl$C_1$-$C_4$alkyl, $C_1$-$C_4$alkoxycarbonyl, cyano; or $R^{10}$ and $R^{11}$ form together an aliphatic heterocyclic group having 5 to 10 ring atoms of which one, two or three are hetero atoms selected from nitrogen, oxygen and sulfur;

$R^{12}$ and $R^{13}$ independently are hydrogen, $C_1$-$C_4$alkyl, $C_2$-$C_4$alkenyl, $C_3$-$C_7$cycloalkyl, $C_3$-$C_7$cycloalkyl$C_1$-$C_4$alkyl, $C_1$-$C_4$alkoxy$C_1$-$C_4$alkyl, hydroxy$C_1$-$C_4$alkoxy$C_1$-$C_4$alkyl, hydroxy$c_1$-$C_4$alkyl, dihydroxy$C_1$-$C_4$alkyl, $C_1$-$C_4$alkoxycarbonyl$C_1$-$C_4$alkyl, $C_1$-$C_4$alkoxycarbonyl, cyano, —$SO_2R^{10}$, —$SO_2N(R^{10})R^{11}$, —S—$R^{10}$, —$SOR^{10}$, —$C_1$-$C_4$-alkylene-$SO_2R^{10}$, —$C_1$-$C_4$-alkylene-$SOR^{10}$, —$C_1$-$C_4$-alkylene-NH—$SO_2R^{10}$, —$C_1$-$C_4$-alkylene-CON($R^{10}$)$R^{11}$, —CON($R^{10}$)$R^{11}$, —$C_1$-$C_4$-alkylene-C(O)O$R^{10}$, fluoroalkyl, or $R^{12}$ and $R^{13}$ form a substituted or unsubstituted aliphatic heterocyclic group having 5 to 10 ring atoms;

$R^{14}$ is NH, $C_1$-$C_4$alkyl-NH—, $C_2$-$C_4$alkenyl-NH—, $C_3$-$C_7$cycloalkyl-NH—, $C_3$-$C_7$cycloalkyl$C_1$-$C_4$alkyl-NH—, $C_1$-$C_4$alkoxy$C_1$-$C_4$alkyl-NH—, hydroxy$C_1$-$C_4$alkoxy$C_1$-$C_4$alkyl-NH—, hydroxy$C_1$-$C_4$alkyl-NH—, dihydroxy$C_1$-$C_4$alkyl-NH—, $C_1$-$C_4$alkoxycarbonyl$C_1$-$C_4$alkyl-NH—, $C_1$-$C_4$alkoxycarbonyl-NH—, —NH—$C_1$-$C_4$-alkylene-CN, —NH—$SO_2R^{10}$), —NH—$SO_2N(R^{10})R^{11}$, —NH—$C_1$-$C_4$-alkylene-S—$R^{10}$, —NH—$SOR^{10}$, —NH—$C_1$-$C_4$-alkylene-$SO_2R^{10}$, —NH—$C_1$-$C_4$-alkylene-$SOR^{10}$), —NH—$C_1$-$C_4$-alkylene-NH—$SO_2R^{10}$, —NH—$C_1$-$C_4$-alkylene-CON($R^{10}$)$R^{11}$, —NH—CON($R^{10}$)$R^{11}$, —NH—$C_1$-$C_4$-alkylene-C(O)O$R^{10}$, —NH-fluoroalkyl, or a substituted or unsubstituted aliphatic heterocyclic group having 5 to 10 ring atoms;

X is O or $CH_2$;

with the proviso that when $R^1$ is either halogen, methyl, ethyl, methoxy, trifluoromethyl or hydrogen and $R^2$, $R^3$, $R^4$ are either hydrogen, methyl or methoxy and $R^5$ is hydrogen or methyl, $R^{12}$ is neither hydrogen, $C_2$-$C_4$alkyl, $C_2$-$C_4$alkenyl, hydroxy$C_1$-$C_4$alkyl, —$C_1$-$C_4$-alkylene-$SO_2R^{10}$, nor —$C_1$-$C_4$-alkylene-$SOR^{10}$;

in free base or acid addition salt form.

Compounds of the invention exist in free or salt, e.g. acid addition salt form. The invention is to be understood as including the compounds of formula I in free as well as in acid addition salt form, e.g. as trifluoroacetate or hydrochloride salt. Suitable pharmaceutically acceptable acid addition salts for pharmaceutical use in accordance with the invention include in particular the hydrochloride salt.

In formula I the following residues are preferred independently, collectively or in any combination or sub-combination:

(a) $R^1$ is hydrogen, chloro, methyl, methoxy, —$CH_2C(O)OCH_3$, —$CH_2CH_2C(O)OCH_3$, —$C(O)N(CH_3)_2$, —$C(O)OCH_3$, cyano, —$SO_2$-1-pyrrolidinyl, —$SO_2CH_3$, —$SO_2NHCH_3$, —$SO_2N(CH_3)_2$, —$SO_2N(CH_3)CH_2COOH$, —S—$CH_3$, —$SOCH_3$ or $R^1$ forms with $R^2$ a —NH—$CH_2$—$CH_2$—$CH_2$— or —CH=CH—CH=CH— ring. $R^1$ is more preferably —$SO_2NHCH_3$;

(b) $R^2$ is hydrogen, chloro, methyl, tri-fluoromethyl, or forms with $R^1$ a —NH—$CH_2$—$CH_2$—$CH_2$—, —CH=CH—CH=CH— ring or with $R^3$ a —CH=CH—CH=CH— ring. More preferably $R^2$ is hydrogen;

(c) $R^3$ is hydrogen, fluoro, methyl, or forms with $R^2$ a —CH=CH—CH=CH— ring. More preferably $R^3$ is hydrogen and chloro;

(d) $R^4$ is hydrogen, chloro, more preferably hydrogen;

(e) $R^5$ is hydrogen, chloro, more preferably hydrogen;

(f) $R^6$ is methyl, hydroxymethyl, —$CH_2$—O—C(O)—N($R^2$)$R^{13}$ and —$CH_2$—X—C(O)—$R^{14}$;

(g) $R^7$ and $R^8$ are methyl;

(h) $R^9$ is ethyl or propyl, more preferably ethyl;

(i) $R^{10}$ is 1-pyrrolidinyl, —$CH_2COOH$, methyl, hydrogen, more preferably methyl;

(k) $R^{11}$ is methyl, hydrogen, more preferably hydrogen;

(l) $R^{12}$ is methyl, ethyl, propyl, 2-hydroxyethyl, 3-hydroxypropyl, 2,3 dihydroxypropyl, 1-(hydroxymethyl)-2-hydroxyethyl, cyano, —$CH_2CH_2$—$SO_2CH_3$, —$CH_2CH_2$—S—$CH_3$, —$CH_2CH_2$—NH—$SO_2CH_3$, —$CH_2C(O)OCH_3$, —$CH_2CONH_2$, 2,2,2-trifluoro-ethyl, or forms with $R^{13}$ a —$CH_2$—$CH_2$—CHOH—$CH_2$—$CH_2$— ring. More preferably $R^{12}$ is ethyl and 2-hydroxyethyl;

(m) $R^{13}$ is hydrogen or forms with $R^{12}$ a —$CH_2$—$CH_2$—CHOH—$CH_2$—$CH_2$— ring;

(n) $R^{14}$ is —NH—CH$_3$, —NH—CH$_2$CH$_3$, —NH—CH$_2$CH$_2$CH$_3$, 2-hydroxyethyl-NH—, 3-hydroxypropyl-NH—, 2,3 dihydroxypropyl-NH—, 1-(hydroxymethyl)-2-hydroxyethyl-NH—, —NH—CH$_2$CN, —NH—CH$_2$CH$_2$—SO$_2$CH$_3$, —NH—CH$_2$CH$_2$—S—CH$_3$, —NH—CH$_2$CH$_2$—NH—SO$_2$CH$_3$, —NH—CH$_2$C(O)OCH$_3$, —NH—CH$_2$CONH$_2$, 2,2,2—NH-trifluoro-ethyl,

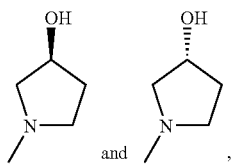

and, more preferably

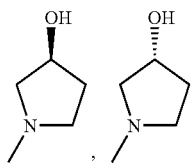

, and 2-hydroxyethyl-NH—;

(o) X is O.

The present invention also provides a process for the production of a compound of formula I or an acid addition salt thereof, comprising (i) for the production of a compound of formula I wherein $R^6$ is —CH$_2$—O—C(O)—N(R$^{12}$)R$^{13}$ and $R^{13}$ is hydrogen, the step of reacting a compound of formula II

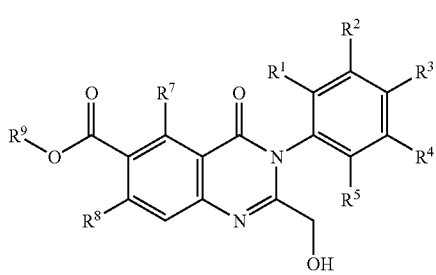

wherein $R^1$, $R^2$, $R^3$, $R^4$, $R^5$, $R^7$, $R^8$, and $R^9$ are as defined above;

with a compound of formula III

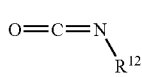

wherein $R^{12}$ is as defined above; or (ii) alternatively to (i) for the production of a compound of formula I wherein $R^6$ is —CH$_2$—O—C(O)—N(R$^{12}$)R$^{13}$ and $R^{13}$ is hydrogen, the step of reacting a compound of formula IV

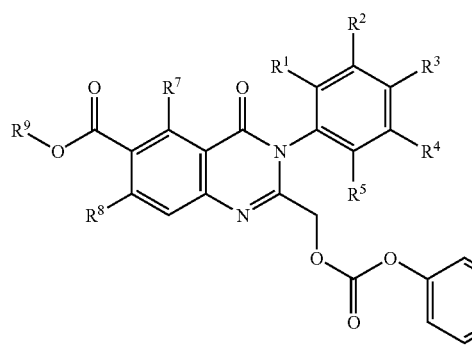

wherein $R^1$, $R^2$, $R^3$, $R^4$, $R^5$, $R^7$ $R^8$, and $R^9$ are as defined above;

with a compound of formula V

wherein $R^{12}$ is as defined above; or (iii) for the production of a compound of formula I wherein $R^6$=—CH$_2$—X—C(O)—R$^{14}$ and X=CH$_2$, the step of reacting a compound of formula VI

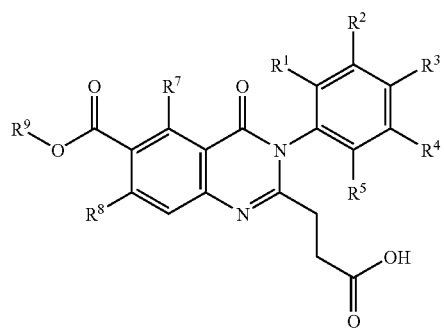

wherein $R^1$, $R^2$, $R^3$, $R^4$, $R^5$, $R^7$, $R^8$ and $R^9$ are as defined above;

with a compound of formula VII

H—R$^{14}$ (VII)

wherein $R^{14}$ is as defined above; or (iv) for the production of a compound of formula I wherein $R^6$=—CH$_2$—X—C(O)—R$^{14}$ and X=O, reacting a compound of formula VIII

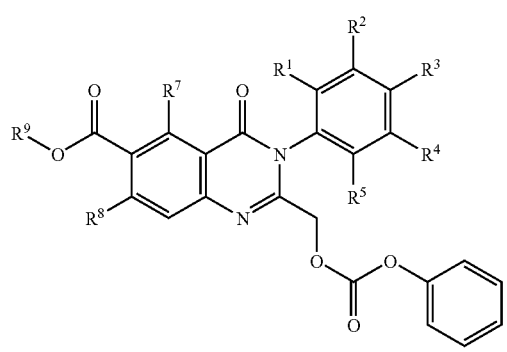

wherein $R^1$, $R^2$, $R^3$, $R^4$, $R^5$, $R^7$, $R^8$, and $R^9$ are as defined above;

with a compound of formula VII; or (v) for the production of a compound of formula I wherein $R^6$ is $C_1$-$C_4$alkyl or hydroxy$C_1$-$C_4$alkyl, the step of reacting a compound of formula IX

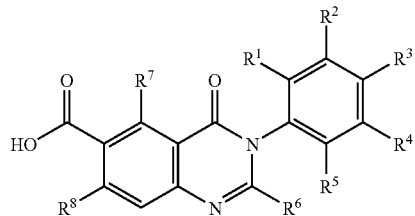

(IX)

wherein $R^1$, $R^2$, $R^3$, $R^4$, $R^5$, $R^7$ and $R^8$ are as defined above and $R^6$ is $C_1$-$C_4$alkyl or hydroxy$C_1$-$C_4$alkyl;
with a compound of formula X $$Y—R^9 \quad (X)$$

wherein $R^9$ is as defined above and Y is a leaving group, e.g. halogen, e.g. Br;
and recovering the so obtained compound of formula I in free base or in acid addition salt form.

Process (i) may be performed according to conventional procedures, e.g. as described in example 1. This process (i) is preferred in cases where the particular isocyanate is commercially available or easily prepared. Processes (ii), (iii), (iv) and (v) may be performed according to conventional procedures, e.g. as described in the relevant examples.

Working up the reaction mixtures and purification of the compounds thus obtained may be carried out in accordance to known procedures.

Acid addition salts may be produced from the free bases in known manner, and vice-versa.

The starting compounds of formulae II, III and V are known or may be produced in analogous manner to known procedures, e.g. as described in example 1. Compounds of formula IV may be produced by reacting a compound of formula II with, e.g. phenyl chloroformate.

The starting compounds of formulae VI, VII, VIII, IX and X are known or may be produced in analogous manner to known procedures, e.g. as described in relevant examples.

The compounds of the invention and their pharmaceutically acceptable acid addition salts, hereinafter referred to as agents of the invention, exhibit valuable pharmacological properties when tested in vitro and in animals, and are therefore useful as pharmaceuticals.

In particular the agents of the invention exhibit cannabinoid (CB) receptor binding activity. More particularly the agents of the invention are active at the human CB1 and CB2 receptor. Cannabinoid receptor interaction of the agents of the invention may be demonstrated by their ability to displace e.g. [$^3$H]CP55940 from human cannabinoid receptors expressed in, e.g. HEK293 or CHOK1 membranes, e.g. as demonstrated in accordance with the following test methods.

Test I: CB1 Receptor Binding Assay

The assay mixture comprises 75 μL of membrane suspension [membranes from HEK293 cells transfected with human CB1 receptors from Receptor Biology, Beltsville, Md.; 133 μg/mL in assay buffer (50 mM Tris-HCl, 2.5 mM EDTA, 5 mM MgCl$_2$ 5 mg/mL BSA, pH7.4), approx. 10 μg/well)], 25 μL WGA-YS beads [Yttrium silicate beads coated with wheat germ agglutinin, Amersham (40 mg/mL, 1 mg/well)], 50 μL test compound in 4% DMSO and 50 μL radioligand {[$^3$H] CP55940 (180 Ci/mmol), New England Nuclear; final concentration 0.125 nM, in assay buffer}. All components are mixed, shaken at room temperature for 2 hours, then counted on a Topcount. Non-saturable binding is measured in the presence of 10 μM (R)-(+)-[2,3-dihydro-5-methyl-3-[(4-morpholinyl)methyl]pyrrolo[1,2,3-de]-1,4-benzoxazin-6-yl] (1-naphthalenyl)methanone (WIN55,212-2, Tocris).

$K_i$ values for the CB1 receptor binding assay are in the range of 1 nM to 100 μM, preferentially from 4 nM to 1 μM for the agents of the invention. The $IC_{50}$ values are calculated in ORIGIN using a logistic fit. $K_i$ values are calculated from the $IC_{50}$ values using the Cheng-Prussoff equation ($K_i$=$IC_{50}$/(1+([L]/$K_d$)) where [L] is the ligand concentration.

Test II: CB2 Receptor Binding Assay

The assay mixture comprises 75 μL of membrane suspension [membranes from CHOK1 cells transfected with human CB2 receptors from Receptor Biology, Beltsville, Md.; 133 μg/mL in assay buffer (50 mM Tris-HCl, 2.5 mM EDTA, 5 mM MgCl$_2$ 5 mg/mL BSA, pH7.4), approx. 10 μg/well)], 25 μL WGA-YS beads [Yttrium silicate beads coated with wheat germ agglutinin, Amersham (40 mg/mL, 1 mg/well)), 50 μL test compound in 4% DMSO and 50 μL radioligand {[$^3$H] CP55940 (180 Ci/mmol), New England Nuclear; final concentration 0.125 nM, in assay buffer}. All components are mixed, shaken at room temperature for 2 hours, then counted on a Topcount. Non-saturable binding is measured in the presence of 10 μM (R)-(+)-[2,3-d]hydro-5-methyl-3-[(4-morpholinyl)methyl]pyrrolo[1,2,3-de]-1,4-benzoxazin-6-yl] (1-naphthalenyl)methanone (WIN55,212-2, Tocris).

$K_i$ values for the CB2 receptor binding assay are also in the range of 1 nM to 100 μM, preferentially from 4 nM to 1 μM for the agents of the invention. The $IC_{50}$ values are calculated in ORIGIN using a logistic fit. $K_i$ values are calculated from the $IC_{50}$ values using the Cheng-Prussoff equation ($K_i$=$IC_{50}$/(1+([L]/$K_d$)) where [L] is the ligand concentration.

The agents of the invention are thus useful in the treatment or prevention of disease conditions in which cannabinoid receptor activation plays a role or is implicated, e.g. in chronic pain, especially inflammatory, e.g. chronic inflammatory pain, inflammatory diseases for example inflammatory airways disease, e.g. Chronic Obstructive Pulmonary Disease (COPD), or in asthma, rhinitis, inflammatory bowel disease, cystitis, e.g. interstitial cystitis, pancreatitis, uveitis, inflammatory skin disorders and rheumatoid arthritis.

Activity specifically as analgesic agents may be confirmed in accordance with standard test methods, e.g. as described in the following test.

Test III: Neuropathic Pain Model

Hyperalgesia is examined in the model of neuropathic pain induced by partial ligation of the sciatic nerve as described by Seltzer et al. (1990). Briefly, Wistar-rats (120-140 g) are anaesthetised, the left sciatic nerve exposed at mid-thigh level through a small incision and ⅓ to ½ of the nerve thickness tightly ligated within a 7.0 silk suture. The wound is closed with a single muscle suture and skin clips and dusted with Aureomycin antibiotic powder. The animals are allowed to recover and used 12-15 days following surgery.

Mechanical hyperalgesia is assessed by measuring paw withdrawal thresholds to an increasing pressure stimulus placed onto the dorsal surface of the paw using an analgesymeter (Ugo-Basile, Milan) with a cut-off of 250 g. Withdrawal thresholds are measured on both the ipsilateral (ligated) and contralateral (unligated) paw prior to (predose) and then up to 6 h following drug or vehicle administration. Data are expressed as withdrawal threshold (g) and percentage reversal of hyperalgesia calculated according to the following formula:

$$\% \text{ reversal} = \frac{\text{ipsilateral threshold postdose} - \text{ipsilateral threshold predose}}{\text{contralateral threshold predose} - \text{ipsilateral threshold predose}} \times 100$$

Potency is expressed as $D_{50}$ value, i.e. the dose of compound necessary to produce 50% reversal of hyperalgesia.

$D_{50}$ values are in the range of 0.1 mg/kg to 100 mg/kg for the agents of the invention.

Activity specifically as CB1 agonists may be confirmed in accordance with standard test methods, e.g. as described in the following test.

Test IV: CB1 Functional Assay

G-protein activation is used as a functional measure of receptor-ligand association for G-protein coupled receptors. The basic mechanism behind G-protein activation is the exchange of bound guanosine 5'-diphosphate (GDP) for guanosine 5'-triphosphate (GTP). Using a radioactive, non-hydrolyzable form of GTP, such as guanosine 5'-O-(3-[$^{35}$S] thiophosphate ([$^{35}$S]GTPγS), G-protein activation is assessed by measuring the accumulation of membrane-bound radioactivity in response to receptor activation.

The assay buffer comprises 25 mM HEPES (2.98 g/0.5 L), 10 mM anhydrous $MgCl_2$ (476 mg/0.5 L), 100 mM NaCl (2.92 g/0.5 L) and 0.1% Bovine Serum Albumin (0.5 g/0.5 L). For a single 96 well plate experiment, all of the following reagents are prepared in assay buffer: 10×GDP (Sodium salt; Sigma, catalogue no. G-7127; 0.004 g/10 mL=10 mM, dilute 1:20 for 500 μM); 10×GTPγS (Tetralithium salt; Sigma, catalogue no. G-8634; 1 mM stock, dilute 1:10 for 100 μM); 10×[$^{35}$S]-GTPγS (NEN Life Science, catalogue no. NEG030H, 250 μCi/20 μL; 10 μM stock, dilute 1:20,000 for 0.5 nM); hCB1 receptor membrane (HEK293 cells; Receptor Biology Inc, catalogue no. RBhCB1 382200), 10 μg per well (stock 9.23 mg/mL, receptor concentration ($B_{max}$): 1.21 μmol/mg protein)=103 μL of cannabinoid supplied membrane in 9497 μL of buffer (the membrane vial is thawed, rapidly diluted with assay buffer and kept on ice); 5×WGA PVT Scintillation Proximity Assay (SPA) Beads (Amersham International, catalogue no. RPNQ001; mg/mL) and 10×Test compound/DMSO control.

The following are pipetted into Packard PicoPlate—96 plates (volumes/wells) to give a total assay volume of 250 μL: 25 μL of 10×(500 μM) GDP or Buffer (for total binding); 25 μL of 10×Test compound/DMSO control; 25 μL of 10×GTPγS (for non specific binding) or Buffer; 25 μL of 10×[$^{35}$S]-GTPγS; 100 μL of Human Cannabinoid receptor (10 μg per well); 50 μL of (20 mg/mL) WGA PVT SPA beads (1 mg per well). The plate is sealed with a topseal A cover and vortexed for 2 minutes. The plate is incubated at room temperature for 60 min., centrifuged (Beckman 6JB) at 800 g for 5 minutes and counted on a Topcount for 3 minutes.

Non-specific binding is determined using 10 μM GTPγS, and this is subtracted from all values. Basal binding is assayed in the absence of agonist and in the presence of GDP. The stimulation by agonist is defined as a percentage increase above basal levels, i.e., $$\{[cpm(agonist)-cpm(no\ agonist)]/cpm(no\ agonist)\} \times 100$$

Data are reported as mean ±S.E.M. of one to six experiments performed in triplicate. Non-linear regression analysis of concentration-response data is performed using Origin version 5, (logistics algorithm; Microcal Software Inc. MA, USA) to calculate percentage maximal effect ($E_{max}$, %) and $EC_{50}$ (nM) values. $E_{max}$ is the maximal activity of the test compound compared to that of WIN55,212-2 on the same plate.

EC50 values are in the range of 1 nM to 50 μM, preferentially from 2 nM to 3 μM for the agents of the invention. $E_{max}$ values are in the range of 52% to 180%, preferentially from 80% to 180% for the agents of the invention.

The agents of the invention are thus in particular useful as cannabinoid receptor agonists, e.g. for the treatment of pain of various genesis or aetiology and as anti-inflammatory and/or anti-oedemic agents for the treatment of inflammatory reactions, diseases or conditions, as well as for the treatment of allergic responses. Having regard to their analgesic/anti-inflammatory profile they are useful for the treatment of inflammatory pain, for the treatment of hyperalgesia and, in particular, for the treatment of severe chronic pain. They are, for example, useful for the treatment of pain, inflammation and/or oedema consequential to trauma, e.g. associated with burns, sprains, fracture or the like, subsequent to surgical intervention, e.g. as post-operative analgesics, as well as for the treatment of inflammatory pain of diverse genesis, e.g. for the treatment of bone and joint pain (osteoarthritis), rheumatoid arthritis, rheumatic disease, teno-synovitis, gout, cancer pain, myofascial pain (muscular injury, fibromyalgia), lower back pain, chronic neuropathic pain, e.g. diabetic neuropathy, phantom limb pain and perioperative pain (general surgery, gynecologic surgery). They are further suitable as analgesics for the treatment of pain associated with, e.g., angina, menstruation or cancer. As anti-inflammatory/anti-oedema agents, they are further useful, e.g., for the treatment of inflammatory skin disorders, for example psoriasis and eczema.

The agent of the invention are also useful for the treatment of chronic psychiatric diseases, such as depressions, depression and bipolar disorders, e.g. manic-depressive psychoses, extreme psychotic states e.g. mania, schizophrenia, and excessive mood swings where behavioural stabilization is desired. In addition, the compound is indicated in ADHD (attention deficit hyperactivity disorders) and other attention disorders, e.g. autism, anxiety states, generalized anxiety and agoraphobia, as well as those behavioural states characterized by social withdrawal e.g. negative symptoms, and for the treatment and prevention of neurodegenerative disease, e.g. Alzheimer, Parkinson.

The agents of the invention are also useful as smooth muscle relaxants, e.g. for the treatment of spasm of the gastrointestinal tract or uterus, e.g. in the therapy of Crohn's disease, ulcerative colitis or pancreatitis and for the treatment of muscle spasticity and tremor in e.g. multiple sclerosis.

Furthermore, the agents of the invention are also useful in the treatment of ocular disorders selected from the group consisting of glaucoma, normal tension glaucoma and neurodegenerative diseases conditions of the retina and the optic nerve, especially in patients presenting risk factors for glaucoma, such as but not exclusively high intraocular pressure, family history of glaucoma, glaucoma in the contralateral eye and high myopia.

Efficacy in said ocular disorders can be established in the following animal models (for a comprehensive discussion of the models see Goldblum and Mittag, Vision Research 42 (2002) 471-478):

(1) experimental glaucoma induced by increased intraocular pressure obtained
  by laser photocoagulation of the trabecular meshwork in rats (Ueda et al., Japan. J. Opthalmol. 1998; 42:337-344), rabbits and monkeys (March et al., Lasers Surg. Med. 1984; 4:329-335, Pederson and Gaasterland, Arch. Opthalmol. 1984; 102:1689-1692)
  by cautery of two or three episcleral/limbal veins in rats (as described in Shareef et al., Exp. Eye Res. 1995; 61: 379-382, Mittag et al., Invest. Opthalmol. Vis. Sci. 2000; 41:3451-3459)

by injection of hypertonic saline into limbal aqueous humor collecting veins of rats (as described in Morrison et al., Exp. Eye Res. 1997; 64: 85-96)

by intraocular injection of alpha-chymotrypsin in rabbits (as described in Fernandez-Durango et al., Exp. Eye Res. 1991; 53: 591-596)

by intraocular injection of S-antigen in rats (Mermoud et al., Graefes Arch. Clin. Exp. Opthalmol. 1994; 232:553-560)

(2) experimental glaucoma induced by optic nerve (ON) injury obtained by ON crush in mice (Levkovitch-Verbin et al., Invest. Opthalmol. Vis. Sci. 2000; 41: 4169-4174) and rats (Yoles and Schwartz, Exp. Neurol. 1998; 153:1-7)

by ON transection in rats (as described in Martin et al., Invest. Opthalmol. Vis. Sci. 2002; 43: 2236-2243, Solomon et al. J. Neurosci. Methods 1996; 70:21-25)

by experimental transient (acute) retinal ischemia in rats after ophthalmic vessel ligature (as described in Lafuente et al., Invest. Opthalmol. Vis. Sci. 2001, 42:2074-2084) or cannulation of the anterior chamber (Buchi et al., Opthalmologica 1991; 203:138-147)

by intraocular endothelin-1 injection in rats (Stokely at al., Invest. Opthalmol. Vis. Sci. 2002; 43: 3223-3230) or rabbits (Takei et al., Graefes Arch. Clin. Exp. Opthalmol 1993; 231:476-481)

(3) experimental glaucoma induced by excitotoxicity in rats (intraocular injection of excitatory amino acids or their analogues as described in Vorwerk et al., Invest. Opthalmol. Vis. Sci. 1996; 37:1618-1624)

(4) spontaneous development of a secondary form (pigment dispersion) of glaucoma in mice (DBA/2J, DBA/2Nnia, and AKXD28/Ty mice as described in Anderson et al., BMC Genetics 2001; 2:1, Chang et al., Nature Genetics 1999; 21: 405-409, John et al., Invest. Opthalmol. Vis. Sci. 1998; 39: 951-962, Sheldon et al., Lab. Animal Sci. 1995; 15:508-518)

In the present description the terms "treatment" or "treat" refer to both prophylactic or preventative treatment as well as curative or disease modifying treatment, including treatment of patients at risk of contracting the disease or suspected to have contracted the disease as well as patients who are ill or have been diagnosed as suffering from a disease or medical condition.

For the above indications the appropriate dosage of the agents of the invention will, of course, vary depending upon, for example, the host, the mode of administration and the nature and severity of the condition being treated as well as the relative potency of the particular agent of the invention employed. For example, the amount of active agent required may be determined on the basis of known in vitro and in vivo techniques, determining how long a particular active agent concentration in the blood plasma remains at an acceptable level for a therapeutic effect. In general, satisfactory results in animals are indicated to be obtained at daily dosages of from about 0.01 to about 20.0 mg/kg p.o. In humans, an indicated daily dosage is in the range of from about 0.7 to about 1400 mg/day p.o., e.g. from about 50 to 200 mg, conveniently administered once or in divided doses up to 4× per day or in sustained release form. Oral dosage forms accordingly suitably comprise from about 0.2 to about 700 mg of an agent of the invention admixed with an appropriate pharmaceutically acceptable diluent or carrier.

The agents of the invention may alternatively be administered e.g. topically in the form of a cream, gel or the like for example for the treatment of conditions of the skin as hereinbefore described or by inhalation, e.g. in dry powder form, for example for the treatment of asthma.

Examples for compositions comprising an agent of the invention include, e.g. a solid dispersion, an aqueous solution, e.g. containing a solubilising agent, a microemulsion and a suspension of, e.g. a hydrochloride salt of a compound of formula I in the range of from 0.1 to 1%, e.g. 0.5%. The composition may be buffered to a pH in the range of, e.g. from 3.5 to 9.5, e.g. to pH 4.5, by a suitable buffer.

The agents of the invention are also useful as research chemicals.

The agents of the invention can be administered in vivo either alone or in combination with other pharmaceutical agents effective in the treatment of diseases and conditions in which CB1 or CB2 receptor activation plays a role or is implicated including cyclooxygenase-2 (COX-2) inhibitors, such as specific COX-2 inhibitors (e.g. celecoxib and rofecoxib) and nonsteroidal anti-inflammatory drugs (NSAIDs) (e.g. acetylsalicylic acid, propionic acid derivatives), vanilloid receptor antagonists, tricyclic antidepressants (e.g. Anafranil®, Asendin®, Aventyl®, Elavil®, Endep®, Norfranil®, Norpramin®, Pamelor®, Sinequan®, Surmontil®, Tipramine®, Tofranil®, Vivactil®, Tofranil-PM®), anticonvulsants (e.g. gabapentin), and $GABA_B$ agonists (e.g. L-baclofen).

The pharmaceutical compositions for separate administration of the combination partners and for the administration in a fixed combination, i.e. a single galenical composition comprising at least two combination partners, according to the invention can be prepared in a manner known per se and are thus suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application.

Novel pharmaceutical compositions contain, for example, from about 0.1% to about 99.9%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In particular, a therapeutically effective amount of each of the combination partners may be administered simultaneously or sequentially and in any order, and the components may be administered separately or as a fixed combination. For example, the method of delay of progression or treatment of a proliferative disease according to the invention may comprise (i) administration of the combination partner (a) in free or pharmaceutically acceptable salt form and (ii) administration of a combination partner (b) in free or pharmaceutically acceptable salt form, simultaneously or sequentially in any order, in jointly therapeutically effective amounts, preferably in synergistically effective amounts, e.g. in daily dosages corresponding to the amounts described herein. The individual combination partners can be administered separately at different times during the course of therapy or concurrently in divided or single combination forms. Furthermore, the term administering also encompasses the use of a pro-drug of a combination partner that converts in vivo to the combination partner as such. The instant invention is therefore to be understood as embracing all such regimes of simultaneous or alternating treatment and the term "administering" is to be interpreted accordingly.

The effective dosage of each of the combination partners employed may vary depending on the particular compound or pharmaceutical composition employed, the mode of administration, the condition being treated, the severity of the condition being treated. Thus, the dosage regimen is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. In general, satisfactory results in animals are indicated to be obtained at daily dosages of from about 0.01 to about 20.0 mg/kg p.o. In humans, an indicated daily dosage is in the range of from about 0.7 to about 1400 mg/day p.o., e.g. from about 50 to 200 mg, conveniently administered once or in divided doses up to 4× per day or in sustained release form. Oral dosage forms accordingly suitably comprise from about 0.2 to about 700 mg.

In accordance with the foregoing, the present invention also provides:
(1) An agent of the invention for use as a cannabinoid receptor agonist, for example for use in any of the particular indications hereinbefore set forth;
(2) A pharmaceutical composition comprising an agent of the invention as active ingredient together with a pharmaceutically acceptable diluent or carrier therefor. Such a composition may be manufactured in a conventional manner.
(2') A pharmaceutical composition for the treatment or prevention of a disease or condition in which cannabinoid receptor activation plays a role or is implicated comprising an agent of the invention and a carrier.
(3) A method for the treatment of any particular indication hereinbefore set forth in a subject in need thereof which comprises administering an effective amount of an agent of the invention;
(3') A method for treating or preventing a disease or condition in which cannabinoid receptor activation plays a role or is implicated comprising administering to a mammal in need thereof a therapeutically effective amount of an agent of the invention.
(4) The use of an agent of the invention for the manufacture of a medicament for the treatment or prevention of a disease or condition in which cannabinoid receptor activation plays a role or is implicated;
(5) A method as defined above comprising co-administration, e.g. concomitantly or in sequence, of a therapeutically effective amount of an agent of the invention and a second drug substance, said second drug substance being for example for use in any of the particular indications hereinbefore set forth.
(6) A combination comprising a therapeutically effective amount of an agent of the invention and a second drug substance, said second drug substance being for example for use in any of the particular indications hereinbefore set forth.

The preferred compound of formula I for use in accordance with the invention is that of Example 2. This compound is a potent CB agonist ($EC_{50}$ in the CB1 functional assay of test IV=0.132±0.019 μM; $E_{max}$=117±5%), in particular CB1 agonist, in vitro ($K_i$ in the CB1 receptor binding assay of test I=0.034±0.003 μM) and CB2 agonist, in vitro ($K_i$ in the CB2 receptor binding assay of test II=0.011±0.0035 μM). The $D_{50}$ value in the neuropathic pain model of test III for the compound of example 2 is 0.5 mg/kg p.o.

Abbreviations used in the examples:
AcOH=Acetic acid; HCl=Hydrochloric acid; KOH=Potassium hydroxide; MeCN=Acetonitrile;
$MgSO_4$=Magnesium sulfate; $Na_2SO_4$=Sodium sulfate; $NaHCO_3$=Sodium hydrogen carbonate;
TFA=Trifluoroacetic acid; THF=Tetrahydrofuran The following examples illustrate the invention.

EXAMPLE 1

Preparation of 2-Ethylcarbamoyloxymethyl-5,7-dimethyl-3-(2-methylsulfamoyl-phenyl)-4-oxo-3,4-dihydro-quinazoline-6-carboxylic acid ethyl ester a) Preparation of 3,5-Dimethyl-benzene-1,2,4-tricarboxylic acid 4-ethyl ester 1,2-dimethyl ester: A yellow, viscous reaction mixture of ethyl isodehydracetate (300 g, 1.53 mol) and dimethyl acetylenedicarboxylate (434.6 g, 3.06 mol) under an argon atmosphere is heated at ca. 190° C. for 1 h. Vigorous $CO_2$ evolution is accompanied by formation of a black reaction mixture. The reaction mixture is allowed to cool to ambient temperature under argon overnight. The mixture is dissolved in ethyl acetate/hexane (ca. 700 mL, 1:2) and purified by filtration through silica gel (5 kg), eluting with hexane/ethyl acetate (3:1) to give the title compound as a yellow oil (427 g, 94.9%).

b) Preparation of 3,5-Dimethyl-benzene-1,2,4-tricarboxylic acid 4-ethyl ester 2-methyl ester: A stirred pale yellow solution of 3,5-dimethyl-benzene-1,2,4-tricarboxylic acid 4-ethyl ester 1,2-dimethyl ester (421 g, 1.43 mol) in methanol (10.2 L) is treated at room temperature with 5M KOH solution (5.74 L) whereupon a light brown solution was formed. The reaction mixture is stirred at room temperature for 35 min, TLC (ethyl acetate: AcOH, 20:1) indicating complete reaction after ca. 15 min. The yellow-brown reaction mixture is treated with ice (3 kg) and extracted with tert-butyl methyl ether (2×15 L). The organic phase is additionally extracted with brine (5 L). Concentrated HCl solution (2.5 L) is added to the aqueous phase until a pH of 1 was achieved, maintaining the temperature below 30° C. with addition of ice as necessary. The acidified aqueous layer is extracted with ethyl acetate (2×3 L), and the organic phases were backwashed with brine (2 L). The combined organic phases are dried over anhydrous $Na_2SO_4$, filtered and the solvent removed under reduced pressure to afford the title compound as a white crystalline solid (377 g, 94%).

c) Preparation of 4-tert-Butoxycarbonylamino-2,6-dimethyl-isophthalic acid 1-ethyl ester 3-methyl ester: A stirred yellow solution of 3,5-dimethyl-benzene-1,2,4-tricarboxylic acid 4-ethyl ester 2-methyl ester (374 g, 1.33 mol), diphenylphosphoryl azide (734 g, 576 mL, 2.66 mol) and triethylamine (270 g, 371.4 mL, 2.66 mol) in tert-butanol (4.2 L) is heated at reflux for 1.5 h. Vigorous $N_2$ evolution is accompanied by formation of a clear brown solution. The reaction mixture is cooled to ca. 50° C. and evaporated to dryness in vacuo to afford a dark brown oil (1.4 kg). This is re-dissolved in dichloromethane (3 L) and washed sequentially with saturated $NaHCO_3$ solution (2×2 L) and brine (2 L). The combined aqueous layers are back-washed with dichloromethane (1 L). The combined organic layers are dried over anhydrous Na$_2$SO$_4$, filtered and the solvent is removed under reduced pressure to afford a dark brown oil (1.14 kg). The crude product is dissolved in hexane/ethyl acetate (1 L, 1:1) and purified by filtration through silica gel (6 kg), eluting with hexane/ethyl acetate (8:1) to afford the title product as a yellow, waxy solid (441.5 g, 94.2%).

d) Preparation of 4-Amino-2,6-dimethyl-isophthalic acid. 1-ethyl ester 3-methyl ester: A stirred clear yellow solution of 4-tert-butoxycarbonylamino-2,6-dimethyl-isophthalic acid 1-ethyl ester 3-methyl ester (435 g, 1.24 mol) in dichloromethane (825 mL) under nitrogen is treated with TFA (825 mL) at room temperature, whereupon CO$_2$ evolution was observed. After stirring at ambient temperature for ca. 1.5 h, the reaction mixture is evaporated to dryness in vacuo. The residue is re-dissolved in ethyl acetate (2 L) and sequentially washed with water (2 L), 50% NaHCO$_3$ solution (2 L), saturated NaHCO$_3$ solution (2 L) and brine (2 L). The combined aqueous phases are back-washed with ethyl acetate (1 L). The combined organic layers are dried over anhydrous Na$_2$SO$_4$, filtered and the solvent is removed under reduced pressure. The resulting thick pulp is treated with hexane (2 L), cooled to 0° C. with stirring and stirred vigorously for 1 h. The suspension is filtered, washed well with cold hexane and dried at 40° C. to constant weight to afford the title product as a white crystalline solid (231.5 g, 74.4%).

e) Preparation of 4-Amino-2,6-dimethyl-isophthalic acid 1-ethyl ester: A stirred white suspension of 4-amino-2,6-dimethyl-isophthalic acid 1-ethyl ester 3-methyl ester (225 g, 0.89 mol) in methanol (5.9 L) under a nitrogen atmosphere is treated at room temperature with 5M KOH solution (3.58 L). The reaction mixture is heated to ca. 80° C., whereupon a clear, colourless solution is finally formed. After heating for 1 h, the reaction mixture is cooled to ca. 40° C. Methanol is removed under reduced pressure and the remaining aqueous phase is extracted with tert-butyl methyl ether (2×3 L). The organic phase is back-extracted with water (0.5 L). Concentrated HCl solution (2.5 L) is added to the combined aqueous phases until a pH of 1 is achieved, maintaining the temperature below 30° C. with addition of ice as necessary. The acidified aqueous layer is extracted with ethyl acetate (2×3 L), and the organic-phases are backwashed with brine (2 L). The combined organic phases are dried over anhydrous Na$_2$SO$_4$, filtered and the solvent concentrated to a volume of ca. 1 L. The yellow ethyl acetate solution is diluted with hexane (2 L) and stored at 0° C. for 1 h. The resulting white suspension is filtered, thoroughly washed with hexane/ethyl acetate (8:2) and dried at 40° C. to constant weight to afford the title product as a white crystalline solid (194 g, 84.9%). A further 17.8 g (7.8%) can be recovered from the mother liquor.)

f) Preparation of 4-(Benzyloxyacetyl)amino-2,6-dimethyl-isophthalic acid 1-ethyl ester: To a stirred solution of 4-amino-2,6-dimethyl-isophthalic acid 1-ethyl ester (25 g, 0.1054 mol) in anhydrous dichloromethane (250 mL) at ice-bath temperature is added diisopropylethylamine (18 mL, 0.421 mol) in one lot followed by benzyloxyacetyl chloride (Aldrich, 18 mL, 0.1159 mol), dropwise. The reaction mixture is allowed to warm to room temperature overnight. TLC/LCMS analysis indicated that the reaction is complete. The reaction mixture is evaporated to dryness and the residue is partitioned between ethyl acetate and 2 M HCl. The organic phase is separated, dried over anhydrous Na$_2$SO$_4$ and evaporated to give a yellow solid. Recrystallization from cyclohexane/ethyl acetate provides the title compound as a yellow crystalline solid (38.5 g, 0.100 mol, 95%).

g) Preparation of N-Methyl-2-nitro-benzenesulfonamide: To a stirred suspension of 2-nitrobenzenesulfonyl chloride (18.24 g, 0.082 mol) in methanol (35 mL) is added methylamine (2.0 M in THF, 90 mL, 0.18 mol), dropwise, via addition funnel. The reaction mixture is allowed to attain room temperature and is then left overnight. TLC (eluent cyclohexane/ethyl acetate 1/1) indicated that some starting material remained. Additional methylamine (2.0 M in THF, 30 mL) is added and the mixture was stirred for 1 h. TLC then indicated that the reaction is complete. The reaction mixture is evaporated in vacuo and the residue is partitioned between water and ethyl acetate. The organic phase is separated and the aqueous phase is extracted with ethyl acetate. The combined organic phases are washed with saturated aqueous NaHCO$_3$ solution, brine and then dried over anhydrous MgSO$_4$. Evaporation in vacuo provides the title compound as pale yellow crystals (16.91 g, 0.078 mol, 95%).

h) Preparation of 2-Amino-N-methyl-benzenesulfonamide: A solution of N-Methyl-2-nitro-benzenesulfonamide (17 g, 0.078 mol) in anhydrous THF (200 mL) is degassed under house vacuum. Palladium on activated charcoal (10% Pd, 3.7 g) is added and the stirred suspension was flushed with hydrogen (balloon). The suspension is stirred under hydrogen overnight. TLC analysis shows that the reaction is complete. The reaction mixture is then filtered through Celite. The spent catalyst is washed sequentially with ethyl acetate and methanol. Evaporation in vacuo provides the title compound as a viscous, pale brown oil (14.6 g, 100%).

i) Preparation of 2-Benzyloxymethyl-5,7-dimethyl-3-(2-methylsulfamoyl-phenyl)-4-oxo-3,4-dihydro-quinazoline-6-carboxylic acid ethyl ester: To a mechanically-stirred suspension of 4-(Benzyloxyacetyl)amino-2,6-dimethyl-isophthalic acid 1-ethyl ester (27 g, 0.07 mol), 2-amino-N-methyl-benzenesulfonamide (13 g, 0.07 mol) and anhydrous toluene (500 mL) in a three-necked round bottom flask is added phosphorus trichloride (51 mL, 0.56 mol) via an addition funnel. The reaction mixture is stirred at room temperature for 5 minutes and then heated to reflux. After 45 minutes LCMS analysis indicates that the reaction is complete. The suspension is cooled to room temperature and the solution phase is decanted from the solid material. The solution and solid material are worked-up separately. The toluene solution is portioned between ethyl acetate and saturated aqueous NaHCO$_3$ solution with vigorous stirring to give a clear biphasic solution. The organic and aqueous phases are separated and the aqueous phase is extracted (×2) with ethyl acetate. The organic phases are combined, dried over anhydrous Na$_2$SO$_4$, and evaporated in vacuo to give an orange oil. Similarly, the solid material is stirred vigorously with ethyl acetate and saturated aqueous NaHCO$_3$ solution to give a clear biphasic solution. The organic and aqueous phases are separated and the aqueous phase is extracted (×2) with ethyl acetate. The organic phases are combined, dried over anhydrous Na$_2$SO$_4$, and evaporated in vacuo to give an orange oil. Trituration of the orange oils with diethyl ether provides yellow solids, which are removed by filtration, washed with diethyl ether and air-dried to provide the title compound (20 g, 0.037 mol, 53%).

k) Preparation of 2-Hydroxymethyl-5,7-dimethyl-3-(2-methylsulfamoyl-phenyl)-4-oxo-3,4-dihydro-quinazoline-6-carboxylic acid ethyl ester: A solution of 2-Benzyloxymethyl-5,7-dimethyl-3-(2-methylsulfamoyl-phenyl)-4-oxo-3,4-dihydro-quinazoline-6-carboxylic acid ethyl ester (15 g, 0.028 mol) in anhydrous THF (270 mL) is degassed under house vacuum. Palladium on activated charcoal (Acros, 10% Pd, 930 mg) is added and the suspension is flushed with hydrogen (balloon). The suspension is stirred under hydrogen overnight. TLC and LCMS analysis indicates that starting material remained. The reaction mixture is filtered through Celite, and the catalyst is washed sequentially with methanol, DCM and methanol. The filtrate is evaporated to give a cream solid. Trituration with diethyl ether provides a white solid which is removed by filtration and dried under high vacuum to provide the title compound (5.42 g, 0.012 mol, 43%). The ethereal filtrate, which contains un-reacted starting material, is evaporated in vacuo and the residue is subjected to a second cycle of hydrogenation (Pd—C, 920 mg): after stirring overnight under hydrogen TLC/LCMS indicated absence of starting material. The reaction mixture is worked-up as above to provide the title compound as a white solid (4.75 g, 0.01 mol, 38%). Total yield: 10.17 g, 0.022 mol, 82%.

l) Preparation of 2-Ethylcarbamoyloxymethyl-5,7-dimethyl-3-(2-methysulfamoyl-phenyl)-4-oxo-3,4-dihydro-quinazoline-6-carboxylic acid ethyl ester: To a stirred solution of 2-hydroxymethyl-5,7-dimethyl-3-(2-methylsulfamoyl-phenyl)-4-oxo-3,4-dihydro-quinazoline-6-carboxylic acid ethyl ester (1.2 g, 2.70 mmol), in anhydrous THF (2 mL) is added ethyl isocyanate (3 mL) in one lot. The resulting suspension is stirred under argon. After 10 minutes, a clear solution results. After 45 minutes TLC/LCMS analysis indicates complete conversion. The reaction is quenched by the addition of excess methanol and is then evaporated in vacuo to dryness. Purification by flash chromatography on silica (gradient elution with ethyl acetate, 30% to 35% to 65%, in diethyl ether) provides the title compound as a colourless glass (1.36 g, 2.63 mmol, 98%). Mp 102-115° C.; $^1$H NMR (400 MHz, CDCl$_3$) 1.12 (3H, t, J=7 Hz), 1.41 (3H, t, J=8 Hz), 2.43 (3 H, s), 2.66 (3 H, d, J=5 Hz), 2.73 (3 H, s), 3.16 (2 H, m), 4.44 (2H, q J=7 Hz), 4.61 (1 H, d, J=14 Hz), 4.73 (1 H, d, J=14 Hz), 4.90 (1 H, bm) overlapping 4.94 (1 H, bm), 7.47 (2 H, m), 7.70 (1 H, dt, J=1, 8 Hz), 7.78 (1 H, dt, J=2, 8 Hz), 8.10 (1H, d, J=8 Hz); $^1$H NMR (400 MHz, CD$_3$OD) 1.11 (3 H, t, J=7 Hz), 1.42 (3 H, t, J=7 Hz), 2.44 (3 H, s), 2.55 (3 H, s), 2.71 (3 H, s), 3.09 (2 H, q, J=7 Hz), 4.46 (2 H, q, J=7 Hz), 4.58 (1 H, d, J=14 Hz), 4.78 (1H, d, J=14 Hz), 7.48 (1H, s), 7.60 (1H, dd, J=1, 8 Hz), 7.81 (2H, m), 8.12 (1H, dd, J=1, 8 Hz); MS m/z (ES$^+$) 517.1 (M+1, 100%); HPLC: retention time=5.185 min, >96%, column Phenomex-Kingsorb C18, 3 cm×4.6 mm ID, solvent system MeCN/H$_2$O (0.1% TFA), gradient 10 to 90% MeCN, 10 min; Detection 254 nm.

m) Preparation of 2-Ethylcarbamoyloxymethyl-5,7-dimethyl-3-(2-methylsulfamoyl-phenyl)-4-oxo-3,4-dihydro-quinazoline-6-carboxylic acid ethyl ester hydrochloride: 2-Ethylcarbamoyloxymethyl-5,7-dimethyl-3-(2-methylsulfamoyl-phenyl)-4-oxo-3,4-dihydro-quinazoline-6-carboxylic acid ethyl ester (504 mg, 0.976 mmol) is dissolved over 10 minutes with vigorous stirring in absolute ethanol (20 mL). To the clear, colourless solution is added concentrated HCl (70 drops), slowly, via pipette. After 5 minutes a dense, white precipitate forms. After stirring for a further 10 minutes, the suspension is evaporated in vacuo and the residue is dried overnight under high vacuum to provide the hydrochloride salt as fine, colourless needles (511 mg, 0.942 mmol, 97%). Mp 126-130° C.; $^1$H NMR (400 MHz, CD$_3$OD) 1.12 (3 H, t, J=8 Hz), 1.43 (3 H, t, J=7 Hz), 2.48 (3 H, s), 2.56 (3 H, s), 2.73 (3 H, s), 3.13 (2 H, m), 4.48 (2 H, q, J=7 Hz), 4.77 (1 H, d, J=15 Hz), 4.90 (1 H, d, J=15 Hz), 7.59 (1 H, s), 7.68 (1 H, dd, J=1, 8 Hz), 7.88 (2 H, m), 8.15 (1 H, dd, J=2, 8 Hz); MS m/z (ES$^+$) 517.1 (M+1, 100%).

The following compounds of formula I wherein $R^{6b}$ is H, $R^7$ and $R^8$ are methyl, and $R^9$ is ethyl may be prepared by following the procedure of Example 1 but using the appropriate starting materials (Ex=Example; with the following HPLC retention data [min] and ion mass):

| Ex | $R^1$ | $R^2$ | $R^3$ | $R^4$ | $R^5$ | $R^{6a}$ | Ion mass (ion) | RT* [min] |
|---|---|---|---|---|---|---|---|---|
| 3 | —Cl | —H | —H | —Cl | —H | —CH$_2$CH$_3$ | 492.1 [M+] | 6.4 |
| 4 | —CH$_2$C(O)OCH$_3$ | —H | —H | —H | —H | —CH$_2$CH$_3$ | 496 [M + H]+ | 5.37 |
| 5 | —Cl | —H | —H | —H | —Cl | —CH$_2$CH$_3$ | 492.5 [M + H]+ | 6.18 |
| 6 | —SO$_2$—N(CH$_3$)$_2$ | —H | —H | —H | —H | —CH$_2$CH$_3$ | 531.2 [M + H]+ | 5.4 |
| 7 | —Cl | —Cl | —H | —H | —H | —CH$_2$CH$_3$ | 492.5 [M + H]+ | 6.67 |
| 8 | —SO$_2$—CH$_3$ | —H | —H | —H | —H | —CH$_2$CH$_3$ | 502 [M + H]+ | 5.2 |
| 9 | —S—CH$_3$ | —H | —H | —H | —H | —CH$_2$CH$_3$ | 470 [M + H]+ | 6.4 |
| 10 | —CH=CH—CH=CH— | | —H | —H | —CH$_3$ | —CH$_2$CH$_3$ | 488 [M + H]+ | 6.5 |
| 11 | —H | —Cl | —H | —H | —H | —CH$_2$CH$_3$ | 458 [M + H]+ | 4.96 |
| 12 | —SO$_2$—CH$_3$ | —H | —H | —H | —H | —CH$_2$CH$_2$CH$_3$ | 516 [M + H]+ | 5.5 |
| 13 | —CH=CH—CH=CH— | | —H | —H | —H | —CH$_2$CH$_3$ | 474.5 [M + H]+ | 6.21 |
| 14 | cyano | —H | —H | —H | —H | —CH$_2$CH$_3$ | 449.2 [M + H]+ | 5.6 |
| 15 | —S—CH$_3$ | —H | —H | —H | —H | —CH$_2$CH$_2$CH$_3$ | 484 [M + H]+ | 6.3 |
| 16 | —SO—CH$_3$ | —H | —H | —H | —H | —CH$_2$CH$_3$ | 486 [M + H]+ | 5.5 |
| 17 | —CH$_2$CH$_2$—C(O)OCH$_3$ | —H | —H | —H | —H | —CH$_2$CH$_3$ | 510 [M + H]+ | 5.6 |
| 18 | —C(O)OCH$_3$ | —H | —H | —H | —H | —CH$_2$CH$_3$ | 482.5 [M + H]+ | 5.55 |
| 19 | —H | —H | —CH$_3$ | —Cl | —H | —CH$_2$CH$_3$ | 472.1 [M + H]+ | 6.4 |
| 20 | —NH—CH$_2$—CH$_2$—CH$_2$— | | —H | —H | —H | —CH$_2$CH$_3$ | 479.1 [M + H]+ | 6.1 |
| 21 | —C(O)—N(CH$_3$)$_2$ | —H | —H | —H | —H | —CH$_2$CH$_3$ | 495.2 [M + H]+ | 5.5 |
| 22 | —SO$_2$—N(CH$_3$)CH$_2$COOH | —H | —H | —H | —H | —CH$_2$CH$_3$ | 575.2 [M + H]+ | 4.8 |
| 23 | —H | —CH=CH—CH=CH— | | —H | —H | —CH$_2$CH$_3$ | 474.5 [M + H]+ | 6.3 |
| 24 | —H | —CF$_3$ | —H | —H | —H | —CH$_2$CH$_3$ | 492 [M + H]+ | 5.15 |
| 25 | —H | —H | —F | —H | —H | —CH$_2$CH$_3$ | 442 [M + H]+ | 6.2 |

*Column Phenomex-Kingsorb C18, 3 cm × 4.6 mm ID, solvent system MeCN/H$_2$O (0.1% TFA), gradient 10 to 90% MeCN, 10 min; Detection 254 nm.

EXAMPLE 2

Preparation of 2-(2-Hydroxy-ethylcarbamoyloxymethyl)-5,7-dimethyl-3-(2-methylsulfamoyl-phenyl)-4-oxo-3,4-dihydro-quinazoline-6-carboxylic acid ethyl ester To a stirred solution of 2-hydroxymethyl-5,7-dimethyl-3-(2-methylsulfamoyl-phenyl)-4-oxo-3,4-dihydro-quinazoline-6-carboxylic acid ethyl ester (800 mg, 1.79 mmol), in anhydrous pyridine (20 mL) under a nitrogen atmosphere is added phenyl chloroformate (0.566 mL, 4.5 mmol) in one lot. A gelatinous, white precipitate is formed. The stirred reaction mixture is heated to 80° C. After 45 minutes TLC/LCMS analysis indicates completion of the reaction. The reaction is allowed to cool and evaporated in vacuo to dryness. The residue is partitioned between ethyl acetate and 2 M HCl. The organic phase is separated, dried over anhydrous $Na_2SO_4$, and evaporated to give an off-white foam which is dried at high vacuum. The foam is dissolved in anhydrous THF (10 mL) and ethanolamine (2 mL, 33 mmol) is added. The reaction mixture is stirred overnight at room temperature under argon. TLC/LCMS analysis indicates completion of the reaction. The reaction mixture is evaporated in vacuo to dryness and the residue is partitioned between dichloromethane and 2 M HCl. The organic phase is separated, dried over anhydrous $Na_2SO_4$ and evaporated in vacuo to give an orange oil. Purification by flash chromatography on silica (gradient elution with ethyl acetate, 50% to 70% to 90%, in cyclohexane) provides the title compound as colourless crystals after drying at high vacuum (872 mg, 1.64 mmol, 91%). Mp 122-125° C.; $^1$H NMR (400 MHz, $CDCl_3$) 1.41 (3 H, t, J=7 Hz), 2.30 (1 H, bm), 2.43 (3 H, s), 2.67 (3 H, d, J=5 Hz), 2.74 (3 H, s), 3.27 (2 H, m), 3.66 (2 H, bm), 4.45 (2 H, q, J=7 Hz), 4.73 (2 H, m), 4.97 (1 H, bm), 5.31 (1 H, bm), 7.45 (1 H, d, J=8 Hz), 7.49 (1 H, s), 7.71 (1 H, t, J=8 Hz), 7.79 (1 H, m), 8.10 (1 H, d, J=8 Hz); MS m/z (ES$^+$) 533.2 (M+1, 100%); HPLC: retention time=4.313 min, >99%, column Phenomex-Kingsorb C18, 3 cm×4.6 mm ID, solvent system MeCN/$H_2O$ (0.1% TFA), gradient 10 to 90% MeCN, 10 min; Detection 254 nm.

The following compounds of formula I wherein $R^6$ is $-CH_2-O-C(O)-NH-R^{12}$, $R^7$ and $R^8$ are methyl, and $R^9$ is ethyl may be prepared by following the procedure of Example 2 but using the appropriate starting materials (Ex=Example; with the following HPLC retention data [min] and ion mass):

| Ex | $R^1$ | $R^2$ | $R^3$ | $R^4$ | $R^5$ | $R^{12}$ | Ion mass (ion) | RT* [min] |
|---|---|---|---|---|---|---|---|---|
| 26 | $-SO_2-$N-1-pyrrolidinyl | $-H$ | $-H$ | $-H$ | $-H$ | $-CH_2CH_2-OH$ | 573.2 [M + H]+ | 4.95 |
| 27 | $-Cl$ | $-H$ | $-H$ | $-H$ | $-H$ | $-CH_2CH_2-S-CH_3$ | 504.4 [M+] | 6.3 |
| 28 | $-SO_2-N(CH_3)_2$ | $-H$ | $-H$ | $-H$ | $-H$ | $-CH_2CH_2-OH$ | 547 [M + H]+ | 4.57 |
| 29 | $-Cl$ | $-H$ | $-H$ | $-H$ | $-H$ | $-CH_2CF_3$ | 512.5 [M + H]+ | 6.4 |
| 30 | $-SO_2-N(CH_3)_2$ | $-H$ | $-H$ | $-H$ | $-H$ | $-CH_2CH_2CH_2-OH$ | 561 [M + H]+ | 4.7 |
| 31 | $-Cl$ | $-H$ | $-H$ | $-H$ | $-H$ | $-CH_2-C(O)OCH_3$ | 502.4 [M + H]+ | 5.75 |
| 32 | $-Cl$ | $-H$ | $-H$ | $-H$ | $-Cl$ | $-CH_2CH_2-SO_2-CH_3$ | 570 [M+] | 5.6 |
| 33 | $-Cl$ | $-H$ | $-H$ | $-H$ | $-H$ | $-CH_2C(O)NH_2$ | 487.5 [M + H]+ | 4.7 |
| 34 | $-SO_2-N(CH_3)_2$ | $-H$ | $-H$ | $-H$ | $-H$ | $-CH_2-CHOH-CH_2-OH$ | 577.2 [M + H]+ | 4.5 |
| 35 | $-Cl$ | $-H$ | $-H$ | $-H$ | $-H$ | $-CH_2CH_2-SO_2CH_3$ | 536.5 [M+] | 5.3 |
| 36 | $-SO_2-N(CH_3)_2$ | $-H$ | $-H$ | $-H$ | $-H$ | $-CH(CHOH)_2$ | 577 [M + H]+ | 4.3 |
| 37 | $-Cl$ | $-H$ | $-H$ | $-H$ | $-H$ | $-CH_2CH_2-NH-SO_2CH_3$ | 551.7 [M+] | 5.19 |
| 38 | $-SO_2-NHCH_3$ | $-H$ | $-H$ | $-H$ | $-H$ | $-C(CH_3)_2CH_2OH$ | 561 [M + H]+ | 5.3 |
| 39 | $-SO_2-NHCH_3$ | $-H$ | $-H$ | $-H$ | $-H$ | $-CH_2CH_2-OH$ | 547.1 [M + H]+ | 5.1 |
| 40 | $-SO_2-NHCH_3$ | $-H$ | $-H$ | $-H$ | $-H$ | $-CH(CH_3)-OH$ | 547.0 [M + H]+ | 4.5 |
| 41 | $-SO_2-NHCH_3$ | $-H$ | $-H$ | $-H$ | $-H$ | $-CH(CH_3)-OH$ (stereo) | 547.0 [M + H]+ | 4.9 |
| 42 | $-SO_2-NHCH_3$ | $-H$ | $-H$ | $-H$ | $-H$ | $-CH(CH_3)-OH$ (stereo) | 547.0 [M + H]+ | 4.8 |
| 43 | $-SO_2-NHCH_3$ | $-H$ | $-H$ | $-H$ | $-H$ | $-CH_2CH_2-S-CH_3$ | 563.4 [M + H]+ | 6.0 |
| 44 | $-SO_2-NH-CH_2C(O)OCH_3$ | $-H$ | $-H$ | $-H$ | $-H$ | $-CH_2CH_3$ | 609.0 [M + H]+ | 6.4 |
| 45 | $-SO_2-NHCH_3$ | $-H$ | $-H$ | $-H$ | $-H$ | $-CH(CH_3)-CH_2-OH$ | 547.1 [M + H]+ | 4.9 |
| 46 | $-SO_2-NHCH_3$ | $-H$ | $-H$ | $-H$ | $-H$ | $-CH_2-C(CH_3)_2-CH_2-OH$ | 575.0 [M + H]+ | 5.5 |
| 47 | $-SO_2-NHCH_3$ | $-H$ | $-H$ | $-H$ | $-H$ | $-C(CH_3)_2-CH_2-OH$ | 561.0 [M + H]+ | 5.3 |

-continued

| Ex | R¹ | R² | R³ | R⁴ | R⁵ | R¹² | Ion mass (ion) | RT* [min] |
|---|---|---|---|---|---|---|---|---|
| 48 | —SO₂—NHCH₃ | —H | —H | —H | —H | 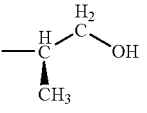 | 547.5 [M + H]+ | 5.0 |
| 49 | —SO₂—NHCH₂—CH₃ | —H | —H | —H | —H | —CH₂CH₂—OH | 547.1 [M + H]+ | 5.1 |
| 50 | —SO₂—NHCH₃ | —H | —H | —H | —H | —CH₂CH₂—O—CH₃ | 547.0 [M + H]+ | 5.6 |
| 51 | —SO₂—NHCH₂CH₂CH₃ | —H | —H | —H | —H | —CH₂CH₂—OH | 561.2 [M + H]+ | 5.6 |
| 52 | —SO₂—NHCH₃ | —H | —H | —H | —H | —CH(CH₂—OH)₂ | 563.0 [M + H]+ | 5.1 |
| 53 | —SO₂—NHCH₃ | —H | —H | —H | —H | —CH₂CN | 528.0 [M + H]+ | 5.5 |
| 54 | —SO₂—NHCH₃ | —H | —H | —H | —H | —CH₂—C(O)NH₂ | 546.4 [M + H]+ | 4.5 |
| 55 | —SO₂—NHCH₃ | —H | —H | —H | —H | —CH₂C(CH₃)₂OH | 561.2 [M + H]+ | |
| 56 | —SO₂—NHCH(CH₃)₂ | —H | —H | —H | —H | —CH₂CH₂—OH | 561.2 [M + H]+ | |
| 57 | 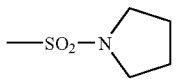 | —H | —H | —H | —H | —CH₂CH₃ | 557.2 [M + H]+ | 7.4 |
| 58 | —SO₂—NHCH₂CH₃ | —H | —H | —H | —H | 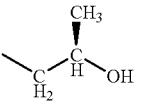 | 561.2 [M + H]+ | |
| 59 | —SO₂—NHCH₂CH₃ | —H | —H | —H | —H | 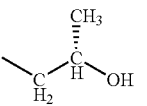 | 561.2 [M + H]+ | |
| 60 | —SO₂—NHCH₃ | —H | —H | —H | —H | 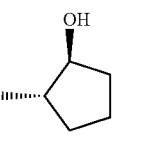 | 573.0 [M + H]+ | |
| 61 | —SO₂—NHCH₃ | —H | —H | —H | —H | 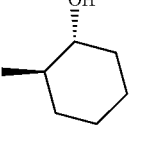 | 587.0 [M + H]+ | 7.3 |
| 62 | —SO₂—NHCH₂CH₃ | —H | —H | —H | —H | 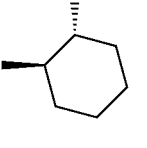 | 601.0 [M + H]+ | 6.8 |
| 63 | —SO₂—NH—CH₃ | —H | —H | —H | —H | 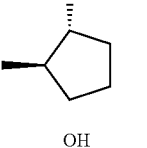 | 573.1 [M + H]+ | 6.3 |
| 64 | —SO₂—NH—CH₂CH₃ | —H | —H | —H | —H | 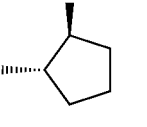 | 587.5 [M + H]+ | 6.5 |

-continued

| Ex | R$^1$ | R$^2$ | R$^3$ | R$^4$ | R$^5$ | R$^{12}$ | Ion mass (ion) | RT* [min] |
|---|---|---|---|---|---|---|---|---|
| 65 | —SO$_2$—NH—CH$_2$CH$_3$ | —H | —H | —H | —H | (trans-2-hydroxycyclopentyl) | 587.4 [M + H]+ | 5.2 |
| 66 | —SO$_2$—NH—CH$_3$ | —H | —H | —H | —H | (trans-2-hydroxycyclopentyl) | 573.2 [M + H]+ | 5.51 |
| 67 | —SO$_2$—NH—CH$_3$ | —H | —H | —H | —H | (cis-2-hydroxycyclopentyl) | 573.1 [M + H]+ | 5.51 |

The following compounds of formula I wherein R$^6$ is —CH$_2$—O—C(O)—N(R$^{12}$)R$^{13}$, R$^7$ and R$^8$ are methyl, and R$^9$ is ethyl may be prepared by following the procedure of Example 2 but using the appropriate starting materials (Ex=Example; with the following HPLC retention data [min] and ion mass):

| Ex | R$^1$ | R$^2$ | R$^3$ | R$^4$ | R$^5$ | R$^{12}$ | R$^{13}$ | Ion mass (ion) | RT* [min] |
|---|---|---|---|---|---|---|---|---|---|
| 69 | —SO$_2$—N(CH$_3$)$_2$ | —H | —H | —H | —H | —CH$_2$—CH$_2$—CHOH—CH$_2$—CH$_2$— | | 587 [M + H]+ | 4.9 |
| 70 | —SO$_2$—NHCH$_3$ | —H | —H | —H | —H | —CH$_2$—CH$_2$—CHOH—CH$_2$— | | 559.4 [M + H]+ | 4.8 |
| 71 | —SO$_2$—NHCH$_3$ | —H | —H | —H | —H | —CH$_2$—CH$_2$—(R)—CHOH—CH$_2$— | | 559.2 [M + H]+ | 4.9 |
| 72 | —SO$_2$—NHCH$_3$ | —H | —H | —H | —H | —CH$_2$—CH$_2$—C(O)—CH$_2$— | | 557.2 [M + H]+ | |
| 73 | —SO$_2$—NHCH$_3$ | —H | —H | —H | —H | —CH$_2$—CH$_2$—CH$_2$—(R)—CH(CH$_2$OH)— | | 573.0 [M + H]+ | 5.5 |
| 74 | —SO$_2$—NHCH$_2$CH$_3$ | —H | —H | —H | —H | —CH$_2$—(R)—CHOH—CH$_2$—CH$_2$— | | 573.2 [M + H]+ | 5 |
| 75 | —SO$_2$—NHCH$_3$ | —H | —H | —H | —H | —CH$_2$—CH$_2$—(S)—CHOH—CH$_2$— | | 559.0 [M + H]+ | 5.9 |
| 76 | —SO$_2$—NHCH$_3$ | —H | —H | —H | —H | —CH$_2$—CH$_2$—CH$_2$—(S)—CHOH—CH$_2$— | | 573.0 [M + H]+ | 6.4 |

Column Phenomex-Kingsorb C18, 3 cm×4.6 mm ID, solvent system MeCN/H$_2$O (0.1% TFA), gradient 10 to 90% MeCN, 10 min; Detection 254 nm.

EXAMPLE 77

Preparation of 3-(2-Chlorophenyl)-2-(2-ethylcarbamoylethyl)-5,7-dimethyl-4-oxo-3,4-dihydroquinazoline-6-carboxylic acid ethyl ester a) 4-(3-Ethoxycarbonylpropionylamino)-2,6-dimethylisophthalic acid 1-ethyl ester: A stirred solution of 4-amino-2,6-dimethylisophthalic acid 1-ethyl ester (0.3 g, 1.26 mmol) and triethylamine (0.355 mL, 2.55 mmol) in dichloromethane (15 mL) at 0° C. is treated with ethyl succinyl chloride (0.199 mL, 1.39 mmol), and the reaction mixture is allowed to warm to room temperature overnight. The reaction mixture is washed with 1 M hydrochloric acid, back-washed with brine and dried over anhydrous MgSO$_4$. The solvent is removed under reduced pressure to afford the title compound, which is used without further purification.

b) 3-(2-Chlorophenyl)-2-(2-ethoxycarbonylethyl)-5,7-dimethyl-4-oxo-3,4-dihydroquinazoline-6-carboxylic acid ethyl ester: A stirred mixture of 4-(3-ethoxycarbonylpropionylamino)-2,6-dimethylisophthalic acid 1-ethyl ester (0.327 g, 0.89 mmol), 2-chloroaniline (0.28 mL, 2.66 mmol) and phosphorus trichloride (0.74 g, 5.4 mmol) in toluene (6 mL) is heated at 130° C. for 3 h. Upon cooling to room temperature, the reaction mixture is poured onto saturated sodium hydrogen carbonate solution and extracted with chloroform. The chloroform extracts are combined, washed with brine and dried over anhydrous MgSO$_4$. The solvent is removed under reduced pressure and the residue is purified by flash chromatography over silica gel (initial eluent: 19:1 cyclohexane:ethyl acetate; final eluent: 7:3 cyclohexane:ethyl acetate) to afford the title compound.

b) 2-(2-Carboxyethyl)-3-(2-chlorophenyl)-5,7-dimethyl-4-oxo-3,4-dihydroquinazoline-6-carboxylic acid ethyl ester: A solution of 3-(2-chlorophenyl)-2-(2-ethoxycarbonylethyl)-5,7-dimethyl-4-oxo-3,4-dihydroquinazoline-6-carboxylic acid ethyl ester (0.1 g, 0.22 mmol) in absolute ethanol (6 mL) is treated with 2M sodium hydroxide solution (12 drops) and the reaction mixture is stirred at room temperature for 4 days. The solvent is removed under reduced pressure, and the residue is dissolved in water and washed with ethyl acetate. The aqueous layer is acidified to pH2 with concentrated hydrochloric acid and this is extracted with ethyl acetate. The organic phases are combined, dried over anhydrous MgSO$_4$ and the solvent is removed under reduced pressure to afford the title compound, which is used without further purification.

c) 3-(2-Chlorophenyl)-2-(2-ethylcarbamoylethyl)-5,7-dimethyl-4-oxo-3,4-dihydroquinazoline-6-carboxylic acid ethyl ester: A mixture of 2-(2-carboxyethyl)-3-(2-chlorophenyl)-5,7-dimethyl-4-oxo-3,4-dihydroquinazoline-6-carboxylic acid ethyl ester (0.093 g, 0.217 mmol), ethylamine hydrochloride (0.018 g, 0.221 mmol), 4-(dimethylamino)pyridine (0.027 g, 0.221 mmol), triethylamine (0.066 g, 0.65 mmol) and 1-[3-(dimethylamino)propyl]-3-ethylcarbodiimide hydrochloride (0.042 g, 0.219 mmol) in dichloromethane (10 mL) is stirred at room temperature for 3 days. The solvent is removed under reduced pressure and the residue is dissolved in ethyl acetate. The ethyl acetate solution is washed sequentially with 2M hydrochloric acid, saturated sodium hydrogen carbonate solution and brine. After drying over anhydrous $MgSO_4$, the solvent is removed under reduced pressure and the residue is purified by preparative high-performance liquid chromatography to afford the title product. $^1H$ NMR (400 MHz, $CDCl_3$): δ 1.13 (3 H, t, J=7.2 Hz), 1.43 (3 H, t, J=7.1 Hz), 2.44 (3 H, s), 2.54-2.62 (2 H, m), 2.70-2.78 (2 H, m), 2.78 (3 H, s), 3.25-3.32 (2 H, m), 4.45 (2 H, q, J=7.3 Hz), 5.98 (1 H, br s), 7.36 (1 H, s), 7.38-7.39 (1 H, m), 7.47-7.49 (2 H, m), 7.61 (1 H, m).

EXAMPLE 78

Preparation of 2-(2-Hydroxy-ethylcarbamoyloxymethyl)-5,7-dimethyl-3-(2-methylsulfamoylphenyl)-4-oxo-3,4-dihydro-quinazoline-6-carboxylic acid propyl ester a) 2-Hydroxymethyl-5,7-dimethyl-3-(2-methylsulfamoylphenyl)-4-oxo-3,4-dihydro-quinazoline-6-carboxylic acid: 2-Benzyloxymethyl-5,7-dimethyl-3-(2-methylsulfamoyl-phenyl)-4-oxo-3,4-dihydro-quinazoline-6-carboxylic acid ethyl ester (3 g, 5.6 mmol) is dissolved in 47% hydrobromic acid. The reaction mixture is stirred at 80° C. overnight, then at 90° C. for 5 h, then at 95° C. for a further 5 h. The reaction mixture is evaporated in vacuo to give a brown solid, which is suspended in diethyl ether/dichloromethane and stirred overnight. Filtration, followed by washing with dichloromethane then ether and drying in vacuo provides the title compound as a sandy brown solid.

b) 2-(2-Hydroxy-ethylcarbamoyloxymethyl)-5,7-dimethyl-3-(2-methylsulfamoylphenyl)-4-oxo-3,4-dihydroquinazoline-6-carboxylic acid propyl ester: To a solution of 2-hydroxymethyl-5,7-dimethyl-3-(2-methylsulfamoylphenyl)-4-oxo-3,4-dihydro-quinazoline-6-carboxylic acid (200 mg, 0.479 mmol) in pyridine (10 mL) is added, in one portion, phenyl chloroformate (0.361 mL, 2.87 mmol) at room temperature. A white precipitate is formed. The reaction mixture is heated to 80° C. for 2 h and is then evaporated and dried at high vacuum. To the residue is added propanol (30 mL) and dichloromethane (1 mL) to give a solution, which is stirred at room temperature overnight. The reaction mixture is evaporated in vacuo to dryness and the residue is partitioned between dichloromethane and 2.0 M hydrochloric acid. The organic phase is dried ($Na_2SO_4$) and evaporated in vacuo to give a yellow oil. The oil is dissolved in THF (5 mL), ethanolamine (1 mL) is added and the reaction mixture is stirred overnight at room temperature. The reaction mixture is evaporated in vacuo to dryness and the residue is partitioned between dichloromethane and 2.0 M hydrochloric acid. The organic phase is dried ($Na_2SO_4$) and evaporated in vacuo to give a yellow oil. Automated gradient elution (10-100% ethyl acetate in hexanes) flash chromatography provides the title compound as a pale yellow foam. $^1H$ NMR (400 MHz, $CDCl_3$): δ 1.02 (3 H, t, J=7 Hz), 1.80 (2 H, m), 2.43 (3 H, s), 2.66 (3 H, d, J=5 Hz), 2.74 (3 H, s), 3.26 (2 H, br m), 3.66 (2 H, br m), 4.44 (2 H, t, J=7 Hz), 4.72 (2 H, m), 5.03 (1 H, br m), 5.43(1 H, br m), 746(2 H, m), 7.71 (1 H, t, J=8 Hz), 779(1 H, t, J=8 Hz), 8.09 (1 H, d, J=8 Hz).

The following compounds of formula I wherein $R^2$, $R^3$, $R^4$ and $R^5$ are H, $R^6$ is —$CH_2$—O—C(O)—$R^{14}$ and $R^7$ and $R^8$ are methyl may be prepared by following the procedure of Example 78 but using the appropriate starting materials (Ex Example; with the following HPLC retention data [min] and ion mass):

| Ex | $R^1$ | $R^{14}$ | $R^9$ | Ion mass (ion) | RT* [min] |
|---|---|---|---|---|---|
| 79 | $SO_2$—$NHCH_2CH_3$ | $NHCH_2CH_2OH$ | $CH(CH_3)_2$ | 561.3 (M + H)+ | 6.46 |
| 80 | $SO_2$—$NHCH_2CH_3$ | $NHCH_2CH_2OH$ | $CH_2CH_2CH_3$ | 561 (M + H)+ | 6.55 |
| 81 | $SO_2$—$NHCH_3$ | $NHCH_2CH_2OH$ | $CH_2CH_2CH_2CH_2CH_3$ | 575 (M + H)+ | 6.23 |
| 82 | $SO_2$—$NHCH_3$ | $NHCH_2CH_2OH$ | $CH(CH_3)_2$ | 547 (M + H)+ | 5.27 |
| 83 | $SO_2$—$NHCH_3$ | 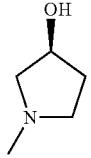 | $CH_2CH_2CH_3$ | 573.1 (M + H)+ | 5.6 |
| 84 | $SO_2$—$NHCH_3$ | 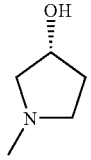 | $CH_2CH_2CH_2CH_2CH_3$ | 601 (M + H)+ | 6.44 |

-continued

| Ex | R¹ | R¹⁴ | R⁹ | Ion mass (ion) | RT* [min] |
|---|---|---|---|---|---|
| 85 | SO$_2$—NHCH$_3$ | (S)-1-methylpyrrolidin-3-ol (3-OH) | CH$_2$CH$_2$CH$_2$CH$_2$CH$_3$ | 601 (M + H)+ | 6.42 |
| 86 | SO$_2$—NHCH$_3$ | (S)-1-methylpyrrolidin-3-ol | CH$_2$CH$_2$CH$_2$CH$_3$ | 587.3 (M + H)+ | 5.95 |
| 87 | SO$_2$—NHCH$_3$ | (R)-1-methylpyrrolidin-3-ol | CH$_2$CH$_2$CH$_2$CH$_3$ | 587.3 (M + H)+ | 5.95 |
| 88 | SO$_2$—NHCH$_3$ | 1-methylpyrrolidin-3-ol | CH$_2$-cyclobutyl | 598.5 (M)+ | 6.1 |
| 89 | SO$_2$—NHCH$_3$ | 1-methylpyrrolidin-3-ol | CH$_2$-morpholinyl | 643 (M)+ | 4.8 |
| 90 | SO$_2$—NHCH$_3$ | 1-methylpyrrolidin-3-ol | CH$_2$-morpholinyl | 643 (M)+ | 4.8 |
| 91 | SO$_2$—NHCH$_3$ | 1-methylpyrrolidin-3-ol | CH$_2$C(O)OC(CH$_3$)$_3$ | 645 (M + H)+ | 6.2 |
| 92 | SO$_2$—NHCH$_3$ | 1-methylpyrrolidin-3-ol | CH$_2$CO$_2$H | 589.1 (M + H)+ | 4.05 |
| 93 | SO$_2$—NHCH$_3$ | CH$_3$NHCH$_2$C(CH$_3$)$_2$OH | CH$_2$-cyclobutyl | 601 (M + H)+ | 6.25 |
| 94 | SO$_2$—NHCH$_3$ | CH$_3$NHCH$_2$C(CH$_3$)$_2$OH | CH$_2$CH$_3$ | 575 (M + H)+ | 6.72 |

-continued

| Ex | $R^1$ | $R^{14}$ | $R^9$ | Ion mass (ion) | RT* [min] |
|---|---|---|---|---|---|
| 95 | $SO_2$—$NHCH_3$ | CH₃NH-CH(OH)-CH— (stereo) | $CH_2$-cyclobutyl | 587.2 (M + H)+ | 6.2 |
| 96 | $SO_2$—$NHCH_3$ | CH₃NH-CH(OH)-CH— (stereo) | $CH_2CH_2CH_3$ | 561.3 (M + H)+ | 5.5 |
| 97 | $SO_2$—$NHCH_3$ | CH₃NH-CH(OH)-CH— (stereo) | $CH_2CH_2CH_3$ | 561.3 (M + H)+ | 5.5 |
| 98 | $SO_2$—$NHCH_3$ | N-methyl-3-hydroxypyrrolidinyl | $CH_2$-cyclobutyl | 599.1 (M + H)+ | 6.2 |
| 99 | $SO_2$—$NHCH_3$ | CH₃NH-CH(OH)-CH— (stereo) | $CH_2$-cyclobutyl | 586.7 (M + H)+ | 6.1 |
| 100 | $SO_2$—$NHCH_3$ | CH₃NH-C(=O)-CH₂— | $CH_2CH_2CH_3$ | 558.65 (M + H)+ | 5.9 |
| 101 | $SO_2$—$NHCH_3$ | CH₃NH-C(=O)-CH₂— | $CH_2$-cyclobutyl | 584.69 (M + H)+ | 6.4 |

HPLC conditions: Phenomenex Luna reverse phase C18 3 micron 30 x 4.9 mm; Gradient elution 10% MeCN in water (+0.08% formic acid) to 100% MeCN over 10 min (rate = 3.0 mL/min; detection = 254 nm).

EXAMPLE 102

2-Hydroxymethyl-5,7-dimethyl-3-(2-methylsulfamoyl-phenyl)-4-oxo-3,4-dihydroquinazoline-6-carboxylic acid butyl ester a) Preparation of 3,5-Dimethyl-benzene-1,2,4-tricarboxylic acid 4-ethyl ester 1,2-dimethyl ester:

A yellow, viscous reaction mixture of ethyl isodehydracetate (300 g, 1.53 mol) and dimethyl acetylenedicarboxylate (434.6 g, 3.06 mol) under an argon atmosphere is heated at ca. 190° C. for 1 h. Vigorous $CO_2$ evolution is accompanied by formation of a black reaction mixture. The reaction mixture is allowed to cool to ambient temperature under argon overnight. The mixture is dissolved in ethyl acetate/hexane (ca. 700 mL, 1:2) and purified by filtration through silica gel (5 kg), eluting with hexane/ethyl acetate (3:1) to give the title compound as a yellow oil.

b) Preparation of 3,5-Dimethyl-benzene-1,2,4-tricarboxylic acid 4-ethyl ester 2-methyl ester: A stirred pale yellow solution of 3,5-dimethyl-benzene-1,2,4-tricarboxylic acid 4-ethyl ester 1,2-dimethyl ester (421 g, 1.43 mol) in methanol (10.2 L) is treated at room temperature with 5M KOH solution (5.74 L) whereupon a light brown solution was formed. The reaction mixture is stirred at room temperature for 35 min, TLC (ethyl acetate: AcOH, 20:1) indicating complete reaction after ca. 15 min. The yellow-brown reaction mixture is treated with ice (3 kg) and extracted with tert-butyl methyl ether (2×15 L). The organic phase is additionally extracted with brine (5 L). Concentrated HCl solution (2.5 L) is added to the aqueous phase until a pH of 1 was achieved, maintaining the temperature below 30° C. with addition of ice as necessary. The acidified aqueous layer is extracted with ethyl acetate (2×3 L), and the organic phases were backwashed with brine (2 L). The combined organic phases are dried over anhydrous $Na_2SO_4$, filtered and the solvent removed under reduced pressure to afford the title compound as a white crystalline solid.

c) Preparation of 4-tert-Butoxycarbonylamino-2,6-dimethyl-isophthalic acid 1-ethyl ester 3-methyl ester: A stirred yellow solution of 3,5-dimethyl-benzene-1,2,4-tricarboxylic acid 4-ethyl ester 2-methyl ester (374 g, 1.33 mol), diphenylphosphoryl azide (734 g, 576 mL, 2.66 mol) and triethylamine (270 g, 371.4 mL, 2.66 mol) in tert-butanol (4.2 L) is heated at reflux for 1.5 h. Vigorous $N_2$ evolution is accompanied by formation of a clear brown solution. The reaction mixture is cooled to ca. 50° C. and evaporated to dryness in vacuo to afford a dark brown oil (1.4 kg). This is re-dissolved in dichloromethane (3 L) and washed sequentially with saturated $NaHCO_3$ solution (2×2 L) and brine (2 L). The combined aqueous layers are back-washed with dichloromethane (1 L). The combined organic layers are dried over anhydrous $Na_2SO_4$, filtered and the solvent is removed under reduced pressure to afford a dark brown oil (1.14 kg). The crude product is dissolved in hexane/ethyl acetate (1 L, 1:1) and purified by filtration through silica gel (6 kg), eluting with hexane/ethyl acetate (8:1) to afford the title product as a yellow, waxy solid.

d) Preparation of 4-Amino-2,6-dimethyl-isophthalic acid 1-ethyl ester 3-methyl ester: A stirred clear yellow solution of 4-tert-butoxycarbonylamino-2,6-dimethyl-isophthalic acid 1-ethyl ester 3-methyl ester (435 g, 1.24 mol) in dichloromethane (825 mL) under nitrogen is treated with TFA (825 mL) at room temperature, whereupon $CO_2$ evolution was observed. After stirring at ambient temperature for ca. 1.5 h, the reaction mixture is evaporated to dryness in vacuo. The residue is re-dissolved in ethyl acetate (2 L) and sequentially washed with water (2 L), 50% $NaHCO_3$ solution (2 L), saturated $NaHCO_3$ solution (2 L) and brine (2 L). The combined aqueous phases are back-washed with ethyl acetate (1 L). The combined organic layers are dried over anhydrous $Na_2SO_4$, filtered and the solvent is removed under reduced pressure. The resulting thick pulp is treated with hexane (2 L), cooled to 0° C. with stirring and stirred vigorously for 1 h. The suspension is filtered, washed well with cold hexane and dried at 40° C. to constant weight to afford the title product as a white crystalline solid.

e) Preparation of 4-Amino-2,6-dimethyl-isophthalic acid 1-ethyl ester: A stirred white suspension of 4-amino-2,6-dimethyl-isophthalic acid 1-ethyl ester 3-methyl ester (225 g, 0.89 mol) in methanol (5.9 L) under a nitrogen atmosphere is treated at room temperature with 5M KOH solution (3.58 L). The reaction mixture is heated to ca. 80° C., whereupon a clear, colourless solution is finally formed. After heating for 1 h, the reaction mixture is cooled to ca. 40° C. Methanol is removed under reduced pressure and the remaining aqueous phase is extracted with tert-butyl methyl ether (2×3 L). The organic phase is back-extracted with water (0.5 L). Concentrated HCl solution (2.5 L) is added to the combined aqueous phases until a pH of 1 is achieved, maintaining the temperature below 30° C. with addition of ice as necessary. The acidified aqueous layer is extracted with ethyl acetate (2×3 L), and the organic phases are backwashed with brine (2 L). The combined organic phases are dried over anhydrous $Na_2SO_4$, filtered and the solvent concentrated to a volume of ca. 1 L. The yellow ethyl acetate solution is diluted with hexane (2 L) and stored at 0° C. for 1 h. The resulting white suspension is filtered, thoroughly washed with hexane/ethyl acetate (8:2) and dried at 40° C. to constant weight to afford the title product as a white crystalline solid. A further amount can be recovered from the mother liquor.

f) Preparation of 4-(Benzyloxyacetyl)amino-2,6-dimethyl-isophthalic acid 1-ethyl ester: To a stirred solution of 4-amino-2,6-dimethyl-isophthalic acid 1-ethyl ester (25 g, 0.1054 mol) in anhydrous dichloromethane (250 mL) at ice-bath temperature is added diisopropylethylamine (18 mL, 0.421 mol) in one lot followed by benzyloxyacetyl chloride (Aldrich, 18 mL, 0.1159 mol), dropwise. The reaction mixture is allowed to warm to room temperature overnight. TLC/LCMS analysis indicated that the reaction is complete. The reaction mixture is evaporated to dryness and the residue is partitioned between ethyl acetate and 2 M HCl. The organic phase is separated, dried over anhydrous $Na_2SO_4$ and evaporated to give a yellow solid. Recrystallization from cyclohexane/ethyl acetate provides the title compound as a yellow crystalline solid.

g) Preparation of N-Methyl-2-nitro-benzenesulfonamide: To a stirred suspension of 2-nitrobenzenesulfonyl chloride (18.24 g, 0.082 mol) in methanol (35 mL) is added methylamine (2.0 M in THF, 90 mL, 0.18 mol), dropwise, via addition funnel. The reaction mixture is allowed to attain room temperature and is then left overnight. TLC (eluent cyclohexane/ethyl acetate 1/1) indicated that some starting material remained. Additional methylamine (2.0 M in THF, 30 mL) is added and the mixture was stirred for 1 h. TLC then indicated that the reaction is complete. The reaction mixture is evaporated in vacuo and the residue is partitioned between water and ethyl acetate. The organic phase is separated and the aqueous phase is extracted with ethyl acetate. The combined organic phases are washed with saturated aqueous $NaHCO_3$ solution, brine and then dried over anhydrous $MgSO_4$. Evaporation in vacuo provides the title compound as pale yellow crystals.

h) Preparation of 2-Amino-N-methyl-benzenesulfonamide: A solution of N-Methyl-2-nitrobenzenesulfonamide (17 g, 0.078 mol) in anhydrous THF (200 mL) is degassed under house vacuum. Palladium on activated charcoal (10% Pd, 3.7 g) is added and the stirred suspension was flushed with hydrogen (balloon). The suspension is stirred under hydrogen overnight. TLC analysis shows that the reaction is complete. The reaction mixture is then filtered through Celite. The spent catalyst is washed sequentially with ethyl acetate and methanol. Evaporation in vacuo provides the title compound as a viscous, pale brown oil.

i) Preparation of 2-Benzyloxymethyl-5,7-dimethyl-3-(2-methylsulfamoyl-phenyl)-4-oxo-3,4-dihydro-quinazoline-6-carboxylic acid ethyl ester: To a mechanically-stirred suspension of 4-(Benzyloxyacetyl)amino-2,6-dimethyl-isophthalic acid 1-ethyl ester (27 g, 0.07 mol), 2-amino-N-methyl-benzenesulfonamide (13 g, 0.07 mol) and anhydrous toluene (500 mL) in a three-necked round bottom flask is added phosphorus trichloride (51 mL, 0.56 mol) via an addition funnel. The reaction mixture is stirred at room temperature for 5 minutes and then heated to reflux. After 45 minutes LCMS analysis indicates that the reaction is complete. The suspension is cooled to room temperature and the solution phase is decanted from the solid material. The solution and solid material are worked-up separately. The toluene solution is partitioned between ethyl acetate and saturated aqueous $NaHCO_3$ solution with vigorous stirring to give a clear biphasic solution. The organic and aqueous phases are separated and the aqueous phase is extracted (×2) with ethyl acetate. The organic phases are combined, dried over anhydrous $Na_2SO_4$, and evaporated in vacuo to give an orange oil. Similarly, the solid material is stirred, vigorously with ethyl acetate and saturated aqueous $NaHCO_3$ solution to give a clear biphasic solution. The organic and aqueous phases are separated and the aqueous phase is extracted (×2) with ethyl acetate. The organic phases are combined, dried over anhydrous $Na_2SO_4$, and evaporated in vacuo to give an orange oil. Trituration of the orange oil with diethyl ether provides a yellow solid, which is removed by filtration, washed with diethyl ether and air-dried to provide the title compound.

k) Preparation of 2-Hydroxymethyl-5,7-dimethyl-3-(2-methylsulfamoyl-phenyl)-4-oxo-3,4-dihydro-quinazoline-6-carboxylic acid ethyl ester: A solution of 2-Benzyloxymethyl-5,7-dimethyl-3-(2-methylsulfamoyl-phenyl)-4-oxo-3,4-dihydro-quinazoline-6-carboxylic acid ethyl ester (15 g, 0.028 mol) in anhydrous THF (270 mL) is degassed under house vacuum. Palladium on activated charcoal (Acros, 10% Pd, 930 mg) is added and the suspension is flushed with hydrogen (balloon). The suspension is stirred under hydrogen overnight. TLC and LCMS analysis indicates that starting material remained. The reaction mixture is filtered through Celite, and the catalyst is washed sequentially with methanol, DCM and methanol. The filtrate is evaporated to give a cream solid. Trituration with diethyl ether provides a white solid which is removed by filtration and dried under high vacuum to provide the title compound. The ethereal filtrate, which contains un-reacted starting material, is evaporated in vacuo and the residue is subjected to a second cycle of hydrogenation (Pd—C, 920 mg): after stirring overnight under hydrogen TLC/LCMS indicated absence of starting material. The reaction mixture is worked-up as above to provide the title compound as a white solid.

l) Preparation of 2-Hydroxymethyl-5,7-trimethyl-3-(2-methylsulfamoyl-phenyl)-4-oxo-3,4-dihydroquinazoline-6-carboxylic acid: 2-Hydroxymethyl-5,7-trimethyl-3-(2-methylsulfamoylphenyl)-4-oxo-3,4-dihydroquinazoline-6-carboxylic acid ethyl ester (1.006 g, 2.3 mmol) is dissolved in 48% hydrobromic acid and the solution is heated at 120° C. for 4.5 h then left to stir at room temperature overnight. The reaction mixture is evaporated in vacuo and the residue is suspended in ethyl acetate. Evaporation of the suspension provided the crude title compound as a pale yellow powder, which is used without further purification.

m) 2-Hydroxymethyl-5,7-dimethyl-3-(2-methylsulfamoyl-phenyl)-4-oxo-3,4-dihydroquinazoline-6-carboxylic acid butyl ester: To a solution of 2-hydroxymethyl-5,7-dimethyl-3-(2-methylsulfamoylphenyl)-4-oxo-3,4-dihydroquinazoline-6-carboxylic acid (238 mg, 0.58 mmol) in DMF (5 mL) at room temperature is added cesium carbonate (187 mg, 0.57 mmol) then, dropwise, 1-bromobutane (0.062 mL, 0.58 mmol). The reaction mixture is stirred at room temperature overnight. The solvent is removed in vacuo and the residue is partitioned between water and ethyl acetate. The aqueous phase is extracted three times with ethyl acetate and the combined organic extracts are dried ($Na_2SO_4$) and evaporated in vacuo. Automated gradient elution (0-80% ethyl acetate in hexanes) flash chromatography provides the title compound as a white solid. $^1$H NMR (400 MHz, $CDCl_3$): δ 0.98 (3 H, t, J=7 Hz), 1.49 (2 H, m), 1.76 (1 H, m), 2.45 (3 H, s), 2.65 (3 H, d, J=5 Hz), 2.75 (3 H, s), 3.98 (1 H, t, J=5 Hz), 4.07 (2 H, d, J=5 Hz), 4.39 (2 H, m), 4.80 (1 H, br t, J=5 Hz), 7.36 (1 H, dd, J=1.5, 8 Hz), 7.50 (1 H, s), 7.76 (2 H, m), 8.14 (1 H, dd, J=1.5, 8 Hz).

EXAMPLE 103

2,5,7-Trimethyl-3-(2-methylsulfamoylphenyl)-4-oxo-3,4-dihydro-quinazoline-6-carboxylic acid cyclobutylmethyl ester a) Preparation of 4-Acetylamino-2,6-dimethyl-isophthalic acid 1-ethyl ester: To a stirred solution of 4-Acetylamino-2,6-dimethyl-isophthalic acid (5 g, 20 mmol) in DCM (50 mL) under argon was added DIPEA (11 mL, 60 mmol). The colourless solution was cooled on an ice bath. Acetic anhydride (2 mL) was added, dropwise. The reaction mixture was left to attain room temperature overnight and the reaction mixture was evaporated in vacuo. To the residue was added ethyl acetate and 2M hydrochloric acid. A white solid precipitated from the biphasic mixture. The white solid was removed by filtration and the organic phase of the filtrate was dried ($Na_2SO_4$) and evaporated in vacuo to give additional white solid. The combined white solids were dried in vacuo to provide the title compound.

b) Preparation of 2,5,7-Trimethyl-3-(2-methylsulfamoyl-phenyl)-4-oxo-3,4-dihydro-quinazoline-6-carboxylic acid ethyl ester: A heterogeneous mixture of 4-Acetylamino-2,6-dimethyl-isophthalic acid 1-ethyl ester (5.39 g, 1.95 mmol), 2-amino-N-methyl-benzenesulfonamide (3.63 g, 1.95 mmol), and phosphorus trichloride (8.5 mL, 9.7 mmol) in toluene (220 mL) was heated at 140° C. (oil bath temperature) for 3.5 h. The reaction mixture was allowed to cool to room temperature and then evaporated in vacuo. Sufficient ethyl acetate was added to dissolve the residue and the solution was washed with saturated aqueous sodium hydrogen carbonate then brine, dried ($Na_2SO_4$) and evaporated in vacuo. Trituration of the residue with dichloromethane gave a white solid, which was removed by filtration. Evaporation of the filtrate solution followed by trituration with ethyl acetate provided a second crop of white solid. The evaporation-trituration procedure was repeated to give two further crops of white solid. The combined white solids were washed with ether and dried in vacuo to provide the title compound.

c) Preparation of Z 5,7-Trimethyl-3-(2-methylsulfamoylphenyl)-4-oxo-3,4-dihydro-quinazoline-6-carboxylic acid: 2,5,7-Trimethyl-3-(2-methylsulfamoyl-phenyl)-4-oxo-3,4-dihydroquinazoline-6-carboxylic acid ethyl ester (1.006 g, 2.3 mmol) is dissolved in 48% hydrobromic acid and the solution was heated at 120° C. for 4.5 h then left to stir at room temperature overnight. The reaction mixture is evaporated in vacuo and the residue is suspended in ethyl acetate. Evaporation of the suspension provided the crude title compound as a pale yellow powder, which is used without further purification.

d) Preparation of 2,5,7-Trimethyl-3-(2-methylsulfamoylphenyl)-4-oxo-3,4-dihydro-quinazoline-6-carboxylic acid cyclobutylmethyl ester: To a solution of 2,5,7-trimethyl-3-(2-methylsulfamoylphenyl)-4-oxo-3,4-dihydro-quinazoline-6-carboxylic acid (196 mg, 0.488 mmol) in DMF (4.5 mL) at ice bath temperature is added, dropwise, sodium hexamethyldisilazide (1.0 M in THF, 0.488 mL). The reaction mixture is allowed to warm to room temperature over 2 h, after which bromomethyl cyclobutane (0.055 mL, 0.488 mmol) is added. After stirring overnight at room temperature, potassium iodide (catalytic quantity) is added and the reaction mixture is heated in a sealed tube to 90° C. in a single mode microwave instrument for 1 h 25 min. The solvent is removed in vacuo and the residue is partitioned between saturated aqueous sodium hydrogen carbonate and ethyl acetate. The organic phase is dried ($Na_2SO_4$) and evaporated in vacuo. Automated gradient elution (10-80% ethyl acetate in hexanes) flash chromatography provides the title compound as a white solid. $^1$H NMR (400 MHz, $CDCl_3$): δ 1.87 (2 H, m), 1.94 (2 H, m), 2.13 (2 H, m) overlapping 2.18 (3 H, s), 2.42 (3 H, s), 2.65 (3 H, d, J=5 Hz), 2.73 (3 H, s) overlapping 2.77 (1 H, m), 4.35 (2 H, d, J=5 Hz), 4 82 (1 H, br m), 7.35 (1 H, dd, J=1, 8 Hz), 7 41 (1 H, s), 7.71 (1 H, m), 778 (1 H, m), 8.14 (1 H, dd, J=1.5, 8 Hz).

The following compounds of formula I wherein $R^1$ is $SO_2$—$NHCH_3$, $R^2$, $R^3$, $R^4$ and $R^5$ are H, and $R^7$ and $R^8$ are methyl may be prepared by following the procedure of Example 102 or 103 but using the appropriate starting materials (Ex=Example; with the following HPLC retention data [min] and ion mass):

| Ex | $R^6$ | $R^9$ | Ion mass (ion) | RT* [min] |
|---|---|---|---|---|
| 104 | $CH_2OH$ | $CH_2CH_2CH_3$ | 459.6 (M+) | 5.6 |
| 105 | $CH_2OH$ | $CH_2$—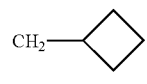 | 486.1 (M + H)+ | 6.3 |
| 106 | $CH_2OH$ | $CH_2$—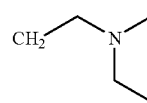 | 531 (M + H)+ | 0.96 |
| 107 | $CH_3$ | $CH_2CH_2CH_2CH_3$ | 458.2 (M + H)+ | 6.6 |

-continued

| Ex | $R^6$ | $R^9$ | Ion mass (ion) | RT* [min] |
|---|---|---|---|---|
| 108 | $CH_3$ | $CH_2CH_2CH_2CH_2CH_3$ | 472 (M + H)+ | 7.03 |
| 109 | $CH_3$ | $CH_2$—△ | 456.1 (M + H)+ | 6 |
| 110 | $CH_3$ | $CH_2CH_2OCH_2CH_3$ | 473.4 (M + H)+ | 5.5 |
| 111 | $CH_3$ | $CH_2CH(CH_3)_2$ | 457.4 (M + H)+ | 6.47 |
| 112 | $CH_3$ | $CH_2$—CH$_2$—N(morpholine) | 515.15 (M + H)+ | 2.5 |

*HPLC conditions: Phenomenex Luna reverse phast C18 3 micron 30 × 4.9 mm; Gradient elution 10% MeCN in water (+0.08% formic acid) to 100% MeCN over 10 min (rate = 3.0 mL/min; detection = 254 nm).

The invention claimed is:

1. A compound of formula I

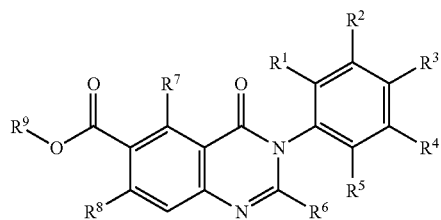

(I)

wherein $R^1$ is —S(=O)$_2$—N(H)—CH$_3$;

$R^2$, $R^3$, $R^4$ and $R^5$ independently are hydrogen; halogen; $C_1$-$C_4$alkyl; $C_2$-$C_4$alkenyl; $C_3$-$C_7$cycloalkyl; $C_3$-$C_7$cycloalkylC$_1$-$C_4$alkyl; $C_1$-$C_4$alkoxyC$_1$-$C_4$alkyl; $C_1$-$C_4$alkylcarboxy; hydroxyC$_1$-$C_4$alkoxyC$_1$-$C_4$alkyl; hydroxyl; hydroxyC$_1$-$C_4$alkyl; phenylC$_1$-$C_4$alkyl which is optionally substituted by hydroxyl, $C_1$-$C_4$alkoxy, carboxy, $C_1$-$C_4$alkoxycarbonylC$_1$-$C_4$alkyl, $C_1$-$C_4$alkoxycarbonyl, or cyano; —SO$_2$R$^{10}$; cyano; —SO$_2$N(R$^{10}$)R$^{11}$; —S—R$^{10}$ or —SOR$^{10}$; or $R^1$ and $R^2$ or $R^2$ and $R^3$ denote, together with the carbon atoms to which they are attached, an aromatic or aliphatic carbocyclic group having 5 to 10 ring atoms or an aromatic or aliphatic heterocyclic group having 5 to 10 ring atoms of which one, two or three are hetero atoms selected from nitrogen, oxygen and sulfur;

$R^6$ is —CH$_2$—O—C(O)—N(R$^{12}$)R$^{13}$, —CH$_2$—X—C(O)—R$^{14}$, $C_1$-$C_4$alkyl or hydroxyC$_1$-$C_4$alkyl;

$R^7$, $R^8$ and $R^9$ independently are $C_1$-$C_4$alkyl;

$R^{10}$ and $R^{11}$ independently are hydrogen, $C_1$-$C_4$alkyl; $C_2$-$C_4$alkenyl; $C_3$-$C_7$cycloalkyl; $C_3$-$C_7$cycloalkylC$_1$-$C_4$alkyl; $C_1$-$C_4$alkoxyC$_1$-$C_4$alkyl; $C_1$-$C_4$alkylcarboxy; hydroxyC$_1$-$C_4$alkoxyC$_1$-$C_4$alkyl; hydroxyl; hydroxyC$_1$-$C_4$alkyl; phenylC$_1$-$C_4$alkyl which is optionally substituted by hydroxyl, $C_1$-$C_4$alkoxy, carboxy, $C_1$-$C_4$alkoxycarbonylC$_1$-$C_4$alkyl, $C_1$-$C_4$alkoxycarbonyl, or cyano; or $R^{10}$ and $R^{11}$ form together an aliphatic heterocyclic group having 5 to 10 ring atoms of which one, two or three are hetero atoms selected from nitrogen, oxygen and sulfur;

$R^{12}$ and $R^{13}$ independently are hydrogen, $C_1$-$C_5$alkyl, $C_2$-$C_4$alkenyl, $C_3$-$C_7$cycloalkyl, $C_3$-$C_7$cycloalkyl C$_1$-$C_4$alkyl, $C_1$-$C_4$alkoxyC$_1$-$C_4$alkyl, hydroxyC$_1$-$C_4$alkoxyC$_1$-$C_4$alkyl, hydroxyC$_1$-$C_4$alkyl, dihydroxyC$_1$-$C_4$alkyl, $C_1$-$C_4$alkoxycarbonylC$_1$-$C_4$alkyl, $C_1$-$C_4$alkoxycarbonyl, cyano, —SO$_2$R$^{10}$, —SO$_2$N(R$^{10}$)R$^{11}$, —S—R$^{10}$, —SOR$^{10}$, —C$_1$-$C_4$-alkylene-SO$_2$R$^{10}$, —C$_1$-$C_4$-alkylene-SOR$^{10}$, —C$_1$-$C_4$-alkylene-NH—SO$_2$R$^{10}$, —C$_1$-$C_4$-alkylene-CON(R$^{10}$)R$^{11}$, —CON(R$^{10}$)R$^{11}$, —C$_1$-$C_4$-alkylene-C(O)OR$^{10}$, fluoroalkyl, —CH$_2$CH$_2$—S—CH$_3$, —CH$_2$CN, or R$^{12}$ and R$^{13}$ form a substituted or unsubstituted aliphatic heterocyclic group having 5 to 10 ring atoms;

$R^{14}$ is NH, $C_1$-$C_4$alkyl-NH—, $C_2$-$C_4$alkenyl-NH—, $C_3$-$C_7$cycloalkyl-NH—, $C_3$-$C_7$cycloalkylC$_1$-$C_4$alkyl-NH—, $C_1$-$C_4$alkoxyC$_1$-$C_4$alkyl-NH—, hydroxyC$_1$-$C_4$alkoxyC$_1$-$C_4$alkyl-NH, hydroxyC$_1$-$C_4$alkyl-NH—, dihydroxyC$_1$-$C_4$alkyl-NH—, $C_1$-$C_4$alkoxycarbonylC$_1$-$C_4$alkyl-NH—, $C_1$-$C_4$alkoxycarbonyl-NH—, —NH—C$_1$-$C_4$-alkylene-CN, —NH—SO$_2$R$^{10}$, —NH—SO$_2$N(R$^{10}$)R$^{11}$, —NH—C$_1$-$C_4$-alkylene-S—R$^{10}$, —NH—SOR$^{10}$, —NH—C$_1$-$C_4$-alkylene-SO$_2$R$^{10}$, —NH—C$_1$-$C_4$-alkylene-SOR$^{10}$, —NH—C$_1$-$C_4$-alkylene-NH—SO$_2$R$^{10}$, —NH—C$_1$-$C_4$-alkylene-CON(R$^{10}$)R$^{11}$, —NH—CON(R$^{10}$)R$^{11}$, —NH—C$_1$-$C_4$-alkylene-C(O)OR$^{10}$, —NH-fluoroalkyl, or a substituted or unsubstituted aliphatic heterocyclic group having 5 to 10 ring atoms;

X is O or CH$_2$;

in free base or acid addition salt form.

2. A compound according to claim 1 of the formula I, which is selected from the group, consisting of the compounds:

2-ethylcarbamoyloxymethyl-5,7-dimethyl-3-(2-methylsulfamoyl-phenyl)-4-oxo-3,4-dihydro-quinazoline-6-carboxylic acid ethyl ester;

2-(2-hydroxy-ethylcarbamoyloxymethyl)-5,7-dimethyl-3-(2-methylsulfamoyl-phenyl)-4-oxo-3,4-dihydro-quinazoline-6-carboxylic acid ethyl ester;

the compounds of the formula I, in which $R^1$ is —S(=O)$_2$—N(H)—CH$_3$, each of $R^2$, $R^3$, $R^4$ and $R^5$ is hydrogen, $R^6$ is —CH$_2$—O—C(=O)—N(H)—R$^{12}$, each of $R^7$ and $R^8$ is methyl, and $R^9$ is ethyl, listed in the following table:

| $R^{12}$ |
|---|
| —C(CH$_3$)$_2$CH$_2$OH |
| 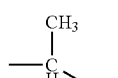 |
|  |
| 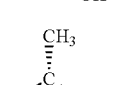 |
| —CH$_2$CH$_2$—S—CH$_3$ |

-continued

| R$^{12}$ |
|---|
| —HC(CH$_2$OH)CH$_3$ (with dashed bond to CH$_3$) |
| —C(CH$_3$)$_2$—CH$_2$—OH |
| —HC(CH$_2$OH)CH$_3$ (with wedge bond to CH$_3$) |
| —CH$_2$CH$_2$—O—CH$_3$ |
| —CH(CH$_2$—OH)$_2$ |
| —CH$_2$CN |
| —CH$_2$—C(O)NH$_2$ |
| —CH$_2$C(CH$_3$)$_2$OH | the compounds of the formula I, in which R$^1$ is —S(=O)$_2$—N(H)—CH$_3$, each of R$^2$, R$^3$, R$^4$ and R$^5$ is hydrogen, R$^6$ is —CH$_2$—O—C(=O)—N(R$^{12}$)—R$^{13}$, each of R$^7$ and R$^8$ is methyl, and R$^9$ is ethyl, listed in the following table:

| R$^{12}$ | R$^{13}$ |
|---|---|
| —CH$_2$—CH$_2$—CHOH—CH$_2$— | |
| —CH$_2$—CH$_2$—(R)—CHOH—CH$_2$— | |
| —CH$_2$—CH$_2$—C(O)—CH$_2$— | |
| —CH$_2$—CH$_2$—CH$_2$—(R)—CH(CH$_2$OH)— | |
| —CH$_2$—CH$_2$—(S)—CHOH—CH$_2$— | |
| —CH$_2$—CH$_2$—CH$_2$—(S)—CHOH—CH$_2$— | |

2-(2-hydroxy-ethylcarbamoyloxymethyl)-5,7-dimethyl-3-(2-methylsulfamoyl-phenyl)-4-oxo-3,4-dihydro-quinazoline-6-carboxylic acid propyl ester, the compounds of the formula I, in which R$^1$ is —S(=O)$_2$—N(H)—CH$_3$, each of R$^2$, R$^3$, R$^4$ and R$^5$ is hydrogen, R$^6$ is —CH$_2$—O—C(=O)—N(R$^{12}$)—R$^{13}$, and each of R$^7$ and R$^8$ is methyl, listed in the following table:

| N(R$^{12}$)—R$^{13}$ | R$^9$ |
|---|---|
| HN—CH$_2$—C(CH$_3$)$_2$—OH (N-methyl) | CH$_2$CH$_2$CH$_3$ |
| CH$_3$NH—CH$_2$—CH(OH)—CH$_3$ | CH$_2$CH$_2$CH$_3$ |
| CH$_3$NH—CH$_2$—CH(OH)—CH$_3$ | CH$_2$CH$_2$CH$_3$ |

2-hydroxymethyl-5,7-dimethyl-3-(2-methylsulfamoyl-phenyl)-4-oxo-3,4-dihydro-quinazoline-6-carboxylic acid butyl ester, and the compounds of the formula I, in which R$^1$ is —S(=O)$_2$—N(H)—CH$_3$, each of R$^2$, R$^3$, R$^4$ and R$^5$ is hydrogen, and each of R$^7$ and R$^8$ is methyl, listed in the following table

| R$^6$ | R$^9$ |
|---|---|
| CH$_2$OH | CH$_2$CH$_2$CH$_3$ |
| CH$_3$ | CH$_2$CH$_2$CH$_2$CH$_3$ |
| CH$_3$ | CH$_2$CH(CH$_3$)$_2$ | in free base form or in acid addition salt form.

3. A compound according to claim 2 of the formula I, which is 2-ethylcarbamoyloxymethyl-5,7-dimethyl-3-(2-methylsulfamoyl-phenyl)-4-oxo-3,4-dihydro-quinazoline-6-carboxylic acid ethyl ester in free base form or in acid addition salt form.

4. A compound according to claim 2 of the formula I, which is 2-(2-hydroxy-ethylcarbamoyloxymethyl)-5,7-dimethyl-3-(2-methylsulfamoyl-phenyl)-4-oxo-3,4-dihydro-quinazoline-6-carboxylic acid ethyl ester in free base form or in acid addition salt form.

5. A process for the preparation of a compound as defined in claim 1 of the formula I, in free base form or in acid addition salt form, comprising (i) for the preparation of a compound of the formula I, wherein R$^6$ is —CH$_2$—O—C(=O)—N(R$^{12}$)—R$^{13}$, and R$^{13}$ is hydrogen, the step of reacting a compound of the formula

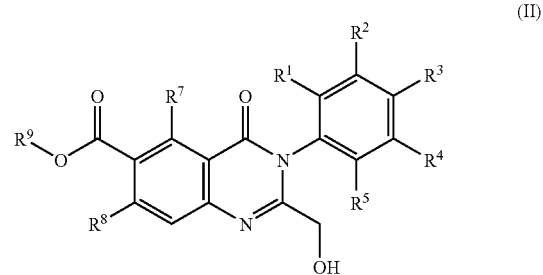

(II)

wherein R$^1$, R$^2$, R$^3$, R$^4$, R$^5$, R$^7$, R$^8$ and R$^9$ are as defined in claim 1, with a compound of the formula

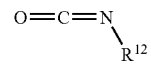

(III)

O=C=N—R$^{12}$ wherein R$^{12}$ is as defined in claim 1; or (ii) alternatively to (i) for the preparation of a compound of the formula I, wherein R$^6$ is —CH$_2$—O—C(=O)—N(R$^{12}$)—R$^{13}$, and R$^{13}$ is hydrogen, the step of reacting a compound of the formula

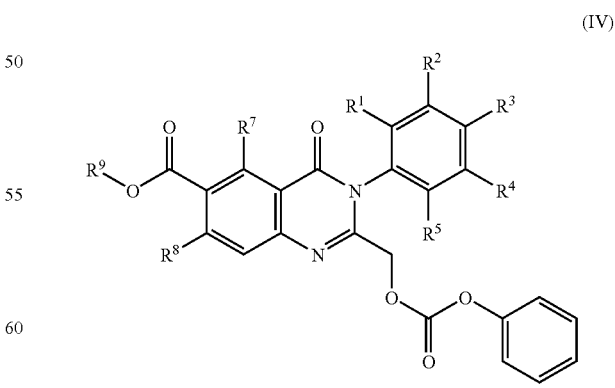

(IV)

wherein R$^1$, R$^2$, R$^3$, R$^4$, R$^5$, R$^7$, R$^8$ and R$^9$ are as defined in claim 1, with a compound of the formula

H$_2$N—R$^{12}$  (V), wherein R$^{12}$ is as defined in claim 1; or (iii) for the preparation of a compound of the formula I, wherein $R^6$ is —$CH_2$—O—C(=O)—$R^{14}$, the step of reacting a compound of the formula

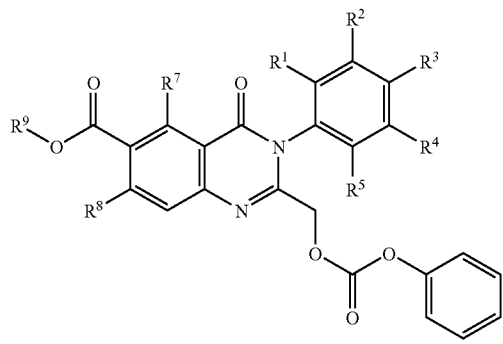

(VIII)

wherein $R^1$, $R^2$, $R^3$, $R^4$, $R^5$, $R^7$, $R^8$ and $R^9$ are as defined in claim 1, with a compound of the formula

 (VII), wherein $R^{14}$ is as defined in claim 1; or (iv) for the preparation of a compound of the formula I, wherein $R^6$ is $C_1$-$C_4$alkyl or hydroxy$C_1$-$C_4$alkyl, the step of reacting a compound of the formula

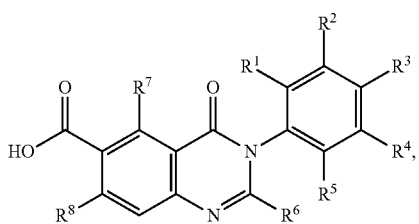

(IX)

wherein $R^1$, $R^2$, $R^3$, $R^4$, $R^5$, $R^7$ and $R^8$ are as defined in claim 1, and $R^6$ is $C_1$-$C_4$alkyl or hydroxy$C_1$-$C_4$alkyl, with a compound of the formula

 (X), wherein $R^9$ is as defined in claim 1, and Y is a leaving group; and recovering the so obtained compound of the formula I in free base form or in acid addition salt form.

6. A pharmaceutical composition comprising a compound as defined in claim 1, in free base form or in pharmaceutically acceptable acid addition salt form, as active ingredient together with a pharmaceutically acceptable diluent or carrier therefor.

* * * * *